(12) United States Patent
Sperry et al.

(10) Patent No.: US 8,691,154 B2
(45) Date of Patent: Apr. 8, 2014

(54) APPARATUS FOR THE GENERATION OF CLEANING AND/OR SANITIZING SOLUTIONS

(75) Inventors: Charles R. Sperry, Leeds, MA (US); Vincent A. Piucci, Southbridge, MA (US); Stephen D. Smith, Williamsburg, MA (US); Dennis F. McNamara, Walpole, NH (US); Suzanne M. Scott, Springfield, VT (US); John Koke, Duncan, SC (US)

(73) Assignee: Diversey, Inc., Sturtevant, WI (US)

( * ) Notice: Subject to any disclaimer, the term of this patent is extended or adjusted under 35 U.S.C. 154(b) by 222 days.

(21) Appl. No.: 13/399,207

(22) Filed: Feb. 17, 2012

(65) Prior Publication Data
US 2013/0216437 A1 Aug. 22, 2013

(51) Int. Cl.
*B01J 19/00* (2006.01)
*A61L 2/00* (2006.01)

(52) U.S. Cl.
USPC ........... 422/111; 422/109; 422/110; 422/122; 422/29

(58) Field of Classification Search
USPC .............................. 422/109, 110, 111, 122, 29
See application file for complete search history.

(56) References Cited

U.S. PATENT DOCUMENTS

| | | | |
|---|---|---|---|
| 2,022,262 A | 11/1935 | White | |
| 4,104,190 A | 8/1978 | Hartshorn | |
| 4,715,983 A | 12/1987 | Ota et al. | |
| 4,748,904 A | 6/1988 | Razeto et al. | |
| 4,874,489 A | 10/1989 | Callerame | |
| 4,932,155 A | 6/1990 | Friemel et al. | |
| 5,008,096 A | 4/1991 | Ringo | |
| 5,091,107 A | 2/1992 | Hutchings | |
| 5,126,070 A | 6/1992 | Leifheit et al. | |
| 5,730,948 A | 3/1998 | Klatte et al. | |
| 5,922,776 A | 7/1999 | Wellinghoff et al. | |
| 5,927,766 A | 7/1999 | Rosen | |
| 5,972,238 A | 10/1999 | Rimpler et al. | |
| 5,980,826 A | 11/1999 | Barenberg et al. | |
| 6,083,457 A | 7/2000 | Parkinson et al. | |
| 6,132,748 A | 10/2000 | Khanna et al. | |
| 6,238,643 B1 | 5/2001 | Thangaraj et al. | |
| 6,294,108 B1 | 9/2001 | Speronello et al. | |

(Continued)

FOREIGN PATENT DOCUMENTS

| | | |
|---|---|---|
| CA | 959238 A | 12/1974 |
| JP | 2002-200488 A | 7/2002 |

(Continued)

OTHER PUBLICATIONS

Safe Ox Chlorine Dioxide Generator Data Sheet, "SafeOx 'Smart' Generator", original document created Sep. 1, 2011, 3 pages.

(Continued)

*Primary Examiner* — Lessanework Seifu
(74) *Attorney, Agent, or Firm* — Nields, Lemack & Frame, LLC

(57) ABSTRACT

The presently disclosed subject matter is directed to an apparatus for the preparation of a cleaning, sanitizing, or sterilizing solution. In some embodiments, the apparatus comprises a modular component, such as a cartridge. The cartridge may contain chemical precursors to allow the generation of chlorine dioxide. The apparatus has a fluid inlet, and separates the fluid into a first flow path, which fills a reservoir. It also has a second flow path, which is heated before passing through the cartridge to create the desired gas. The fluid output from the cartridge is then fed into the reservoir.

20 Claims, 23 Drawing Sheets

(56) References Cited

U.S. PATENT DOCUMENTS

| | | |
|---|---|---|
| 6,383,541 B1 | 5/2002 | Danner et al. |
| 6,399,039 B2 | 6/2002 | Ostgard |
| 6,436,345 B1 | 8/2002 | Roensch et al. |
| 6,451,253 B1 | 9/2002 | Pitochelli et al. |
| 6,468,479 B1 | 10/2002 | Mason et al. |
| 6,602,466 B2 | 8/2003 | Hamilton et al. |
| 6,607,696 B1 | 8/2003 | Hamilton et al. |
| 6,620,380 B2 | 9/2003 | Thomas et al. |
| 6,635,230 B2 | 10/2003 | Klatte |
| 6,645,457 B2 | 11/2003 | Mason et al. |
| 6,676,850 B2 | 1/2004 | Speronello et al. |
| 6,734,157 B2 | 5/2004 | Radwanski et al. |
| 6,764,661 B1 | 7/2004 | Girard |
| 6,890,481 B2 | 5/2005 | Aamodt et al. |
| 6,916,480 B2 | 7/2005 | Anderson et al. |
| 7,087,190 B2 | 8/2006 | Hei et al. |
| 7,150,854 B2 | 12/2006 | Koermer et al. |
| 7,182,883 B2 | 2/2007 | Speronello et al. |
| 7,220,367 B2 | 5/2007 | Speronello et al. |
| 7,229,647 B2 | 6/2007 | Lee et al. |
| 7,273,567 B1 | 9/2007 | Wellinghoff et al. |
| 7,311,884 B2 | 12/2007 | Brownfield et al. |
| 7,383,946 B2 | 6/2008 | Hughes |
| 7,504,074 B2 | 3/2009 | Martens et al. |
| 7,534,398 B2 | 5/2009 | Dee et al. |
| 7,666,384 B2 | 2/2010 | Sanderson |
| 7,695,692 B2 | 4/2010 | Sanderson |
| 7,922,984 B2 | 4/2011 | Hamilton et al. |
| 7,967,958 B2 | 6/2011 | Sano |
| 2002/0020675 A1 | 2/2002 | Herrington et al. |
| 2004/0022676 A1 | 2/2004 | Hamilton et al. |
| 2006/0051285 A1 | 3/2006 | Hawker et al. |
| 2007/0172412 A1 | 7/2007 | Hratko et al. |
| 2007/0231220 A1 | 10/2007 | Agius et al. |
| 2007/0272895 A1 | 11/2007 | Scialla et al. |
| 2008/0127994 A1 | 6/2008 | Rippl et al. |
| 2008/0292507 A1 | 11/2008 | Dee et al. |
| 2008/0299161 A1 | 12/2008 | Sanderson |
| 2009/0078911 A1 | 3/2009 | Shibata et al. |
| 2009/0142235 A1 | 6/2009 | Rico et al. |
| 2009/0263313 A1 | 10/2009 | Martens et al. |
| 2009/0324746 A1 | 12/2009 | Bober et al. |
| 2010/0074813 A1 | 3/2010 | Dee |
| 2011/0129388 A1 | 6/2011 | Alarid et al. |
| 2011/0129390 A1 | 6/2011 | Dee et al. |
| 2012/0012466 A1 | 1/2012 | Sperry et al. |

FOREIGN PATENT DOCUMENTS

| | | |
|---|---|---|
| WO | 03/042111 A2 | 5/2003 |
| WO | 2004/084698 A2 | 10/2004 |
| WO | 2005/011759 A1 | 2/2005 |
| WO | 2007/105885 A1 | 9/2007 |

OTHER PUBLICATIONS

Office Action—Restriction—mailed Apr. 10, 2013 in co-pending U.S. Appl. No. 12/986,248.

Office Action mailed Sep. 27, 2013 in co-pending U.S. Appl. No. 12/986,248.

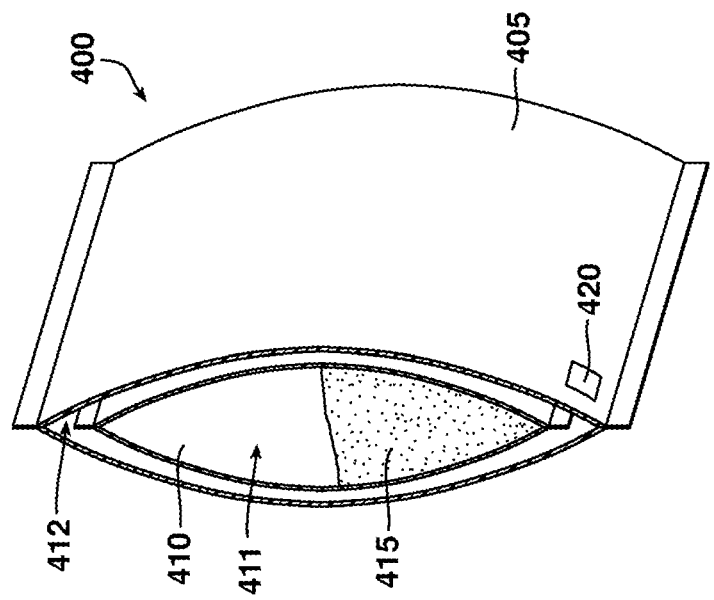
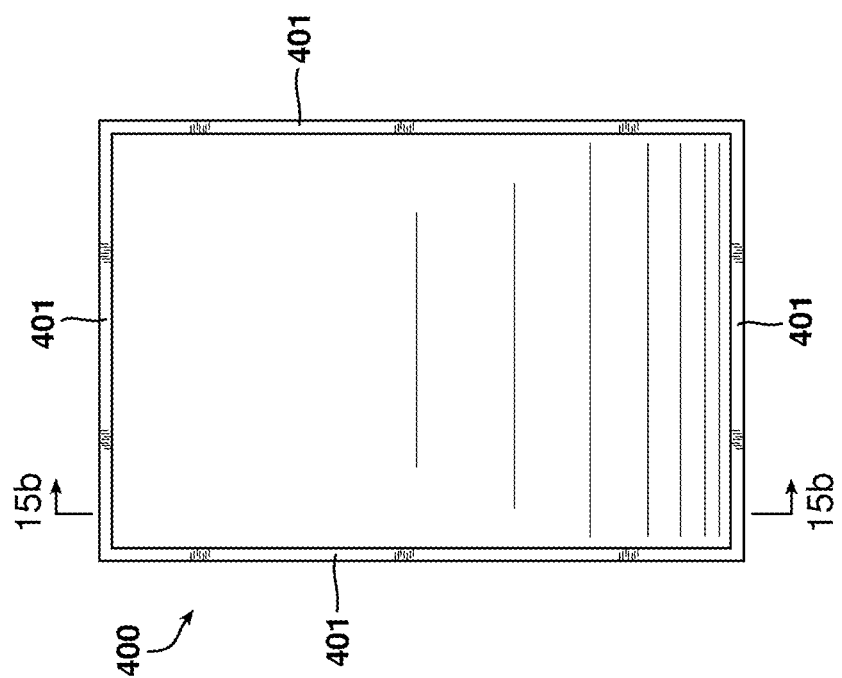

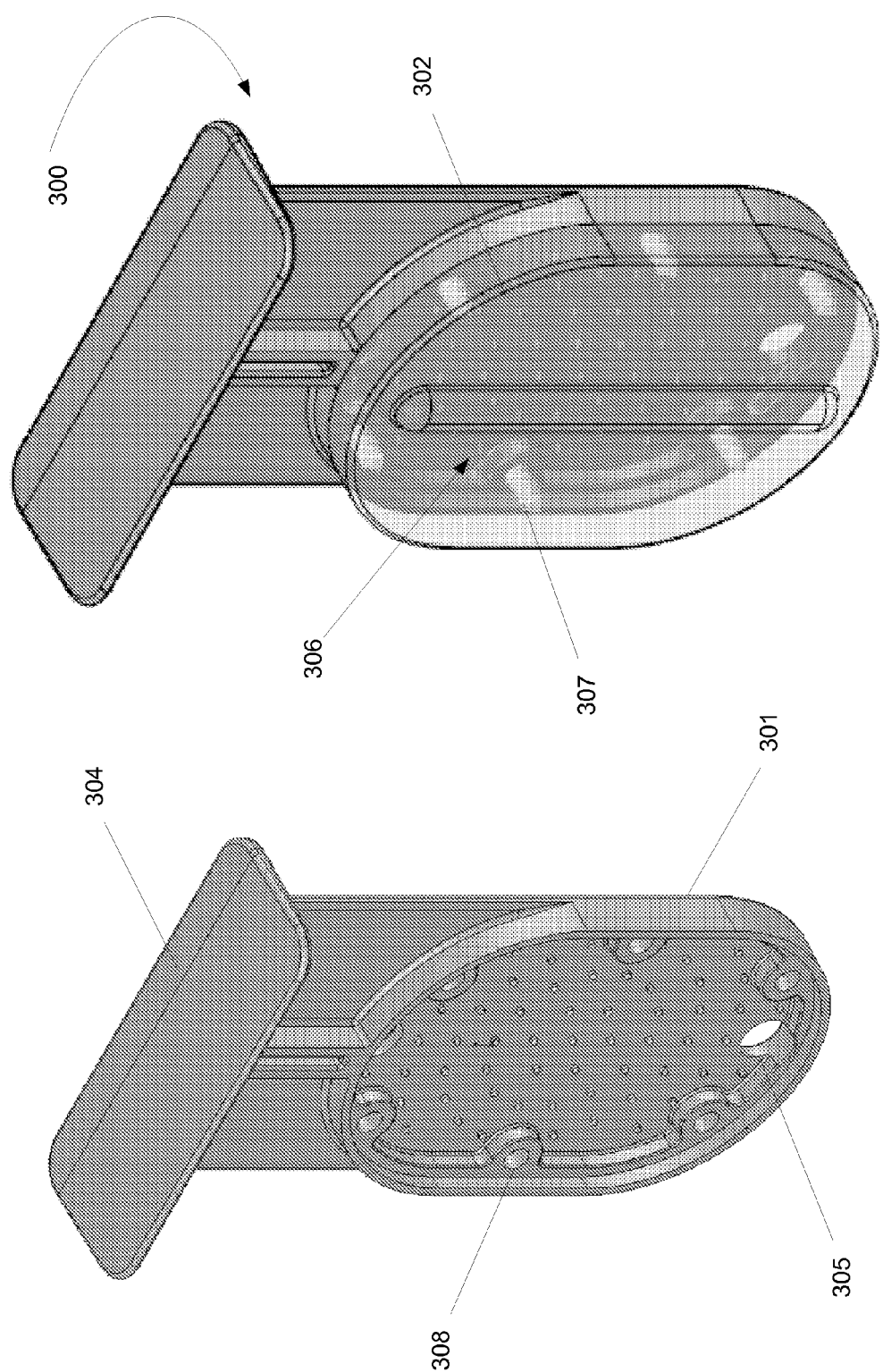

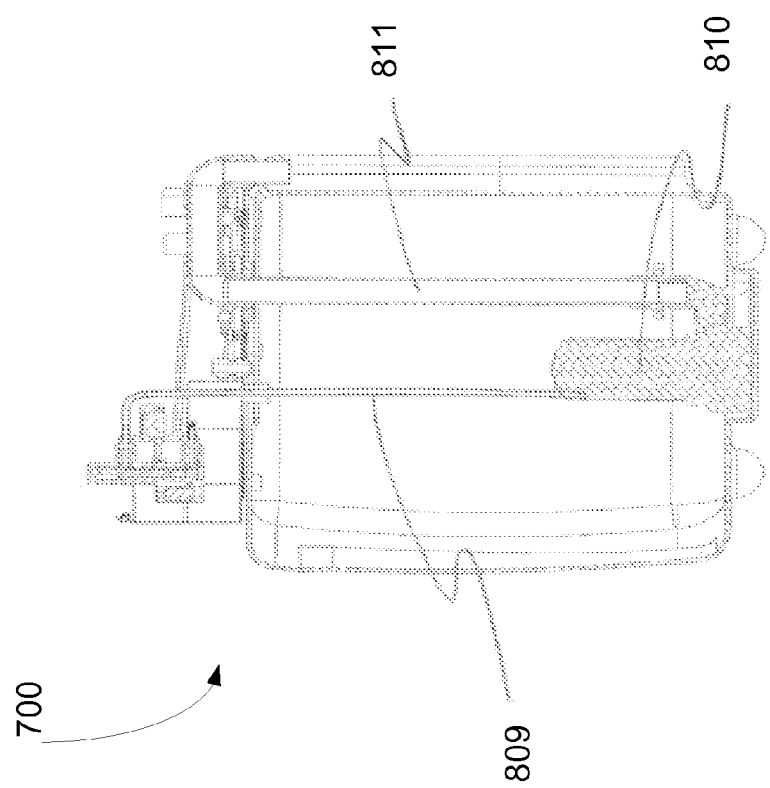

APPARATUS FOR THE GENERATION OF CLEANING AND/OR SANITIZING SOLUTIONS

FIELD OF THE INVENTION

The presently disclosed subject matter relates to a system for producing cleaning and/or sanitizing solutions using a replaceable cartridge, and more specifically, to a system for the production of chlorine dioxide solution.

BACKGROUND

Sterilizing and cleaning solutions are commonly used on a wide variety of surfaces when microbial action against spores, viruses, fungi, and/or bacteria is required. Such sterilizing and cleaning solutions have a broad range of applications in medical, commercial, and household environments to eliminate further microbial growth. For example, sterilizing solutions are commonly used in the preservation of poultry and fish, general agricultural and petrochemical uses, breaking down of biofilms, water treatment, general medical disinfection, and any application where there is a desire to free a surface from living organisms.

In some embodiments, sterilizing and cleaning solutions can be produced electrochemically using an electrolytic cell. However, there are several disadvantages associated with the electrolytic production of these solutions in the prior art. Particularly, the production of corrosive chemicals inside the electrolytic cell can damage the electrodes, thereby limiting cell life. In addition, scale can build up on the electrodes and cell internals. Further, the life of the ion exchange membranes is limited.

Alternatively, in some embodiments, sterilizing and cleaning solutions can be produced chemically by reacting two or more reagents. For example, a chlorine dioxide solution can be produced by chemically reacting sodium chlorite and citric acid in the presence of water or water vapor. However, there are several disadvantages associated with the chemical production of such solutions in the prior art. For example, some solutions (such as chlorine dioxide solutions) must be produced on-site because of instability and short shelf-life. In addition, transport and storage of chemically produced cleaning and/or sterilizing solutions has been found to be impractical.

The presently disclosed system addresses the disadvantages associated with prior art methods and devices for producing sterilizing and cleaning solutions. Particularly, the presently disclosed subject matter employs a cartridge system to facilitate the easy replacement of consumables and wear components. When the cartridge reaches the end of its service life, it is easily removed and replaced. In this manner, none of the consumables are wasted, since all will expire at approximately the same time. In addition, there will be minimal downtime of the device. The disclosed system virtually eliminates the cost and time necessary for service and maintenance of the system as a result of the rapid and simple replacement of the cartridge, and the longevity of the non-cartridge elements.

Thus, the presently disclosed subject matter addresses the problems present in the prior art by disclosing a system for producing a cleaning and/or sterilizing solution. In some embodiments, this is achieved by providing consumables in a quick-change cartridge.

SUMMARY

In some embodiments, the presently disclosed subject matter is directed to an apparatus for the preparation of a cleaning, sanitizing, or sterilizing solution. In some embodiments, the apparatus comprises a modular component, such as a cartridge. The cartridge may contain chemical precursors to allow the generation of chlorine dioxide. The apparatus has a fluid inlet, and separates the fluid into a first flow path, which fills a reservoir. It also has a second flow path, which is heated before passing through the cartridge to create the desired gas. The fluid output from the cartridge is then fed into the reservoir.

BRIEF DESCRIPTION OF THE DRAWINGS

FIG. 2a is a front elevation view of one embodiment of a sachet that can be used in accordance with the presently disclosed subject matter.

FIGS. 2b-2d are perspective sectional views of some embodiments of the sachet of FIG. 2a taken along line 15b-15b.

FIG. 4b is a sectional front elevation view taken along line 17b-17b of FIG. 4a.

FIG. 7a shows the back portion of one embodiment of a cartridge.

FIG. 7b shows the cartridge of FIG. 7a assembled.

FIGS. 10b-c are cross-sections of the apparatus of FIG. 10a, taken along line A-A shown in FIG. 9c.

DETAILED DESCRIPTION

Unlike prior art systems that require significant user interaction, the presently disclosed subject matter is directed to an apparatus for the generation of sanitizing solution, that utilizes a cartridge system. This cartridge system facilitates the easy replacement of consumables and wear components to reliably produce one or more cleaning and/or sanitizing solutions. In addition, the disclosed system may include a cartridge that can comprise the chemical precursors used to generate at least one cleaning and/or sanitizing solution. The disclosed system can employ individual cartridges, cartridges with multiple elements, or a single cartridge that contains all of the consumables. The quantity of each consumable supplied in the cartridge is only enough to last for the chosen design life of the cartridge. This is generally enough for one batch of solution.

When the cartridge reaches the end of its service life, it is easily removed and replaced. In this manner, there is no wasting of the consumables since all will expire at approximately the same time. As a result, there will be minimal downtime of the disclosed system. Thus, the disclosed cartridge system eliminates the cost and time necessary for service and maintenance of the apparatus used to electrochemically and/or chemically generate cleaning and/or sanitizing solutions.

Figure 1A:
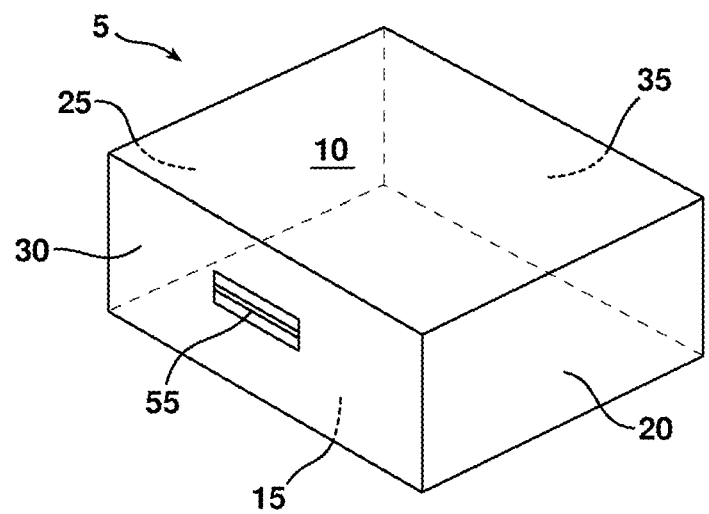
FIGS. 1a-1b are perspective views of an embodiment of cartridge that can be used in accordance with the presently disclosed subject matter.
Figure 1B:
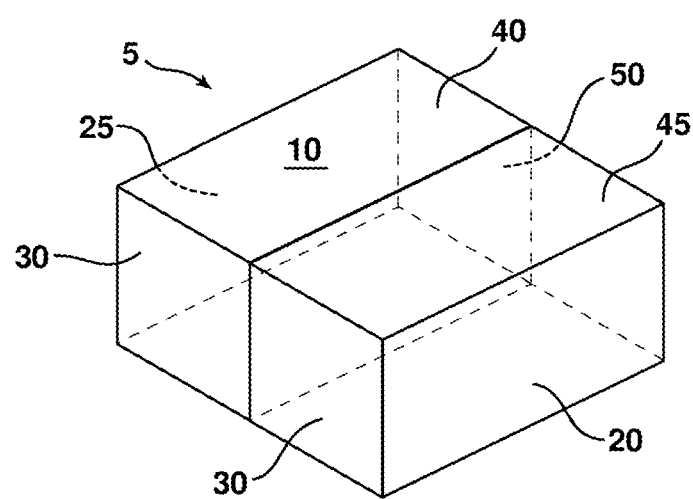

As illustrated in FIG. 1a, cartridge 5 can comprise a top face 10 and a bottom face 15. In some embodiments, the top face 10 and the bottom face 15 can be parallel in relation to each other. Cartridge 5 can further comprise side faces 20, 25, a front face 30, and a rear face 35. In some embodiments, side faces 20 and 25 can be parallel in relation to each other. Similarly, in some embodiments, front and rear faces 30 and 35 can be parallel in relation to each other. Cartridge 5 may contain a closed body having a confined space within the body to enclose one or more consumable components. Thus, cartridge 5 comprises at least one compartment within its interior. To this end, FIG. 1b illustrates one embodiment of a cartridge comprising more than one compartment. Particularly, compartments 40 and 45 are separated by wall 50.

As depicted in FIG. 1a, in some embodiments, cartridge 5 can comprise gripping means 55 that can function as a handle for gripping the cartridge. Any of a wide variety of gripping means known in the art can be incorporated into cartridge 5, including (but not limited to) notches, rods, handles, pull rings, bars, knobs, and the like. One of ordinary skill in the art would recognize that the presently disclosed subject matter also includes embodiments wherein cartridge 5 is configured without a gripping means.

As depicted in FIGS. 1a and 1b, cartridge 5 can be rectangular in shape, although the presently disclosed subject matter is by no means limited to the embodiments illustrated in the Figures. To this end, cartridge 5 can take any shape and form, limited only by its ability to be placed within the disclosed apparatus without interfering with the components housed within the cartridge, as discussed in more detail herein below. Thus, cartridge 5 can be of any size or shape (e.g., square, rectangular, circular, ovoid, elongate, triangular, amorphous, and the like). To this end, the compartments housed within cartridge 5 can likewise take any shape or form.

Cartridge 5 can be constructed from any of a wide variety of materials known in the art, including (but not limited to) plastics (including PVC, polyethylene, polypropylene, other polyolefins, foam plastics, rubberized plastics, and the like), metals (including stainless steel and the like), wood, composite materials (including carbon/graphite, Kevlar®, and fiberglass with an epoxy resin), and the like. For example, in some embodiments, cartridge 5 can be constructed from durable, resilient plastic material that can help to protect the internal components from external impact and forces that might otherwise cause damage.

Cartridge 5 can be constructed in a wide variety of ways. For example, in some embodiments, cartridge 5 can be constructed from molded plastic and can be attached to a housing through the use of adhesives, ultrasonic welding, or mechanical fasteners (such as screws). One of ordinary skill in the art would be familiar with the methods that can be used to construct cartridge 5, and such methods will not be described in detail herein.

In some embodiments, cartridge 5 can comprise a label or other identifier printed or affixed to one or more faces. For example, the identifier can identify the cartridge contents, intended use of the cartridge, and the like. In some embodiments, the identifier can be in the form of a barcode, RFID or other device that can be read and identified by a corresponding reading device built into the apparatus.

In some embodiments, the sanitizing solution can be a chlorine dioxide solution. Chlorine dioxide is generally produced on site because it is an unstable compound with a short shelf life and is not practical to store or transport. To generate chlorine dioxide chemically, two or more chemical precursors and an initiator are required. For example, in some embodiments, the chemical precursors can be sodium chlorite and citric acid, although the presently disclosed subject matter is not limited and can include any reactants that can be combined in the presence of an initiator to generate chlorine dioxide or other sanitizing agents.

In some embodiments, the initiator can be water or water vapor. For example, as discussed in more detail herein below, when sodium chlorite and citric acid are combined in the presence of water or water vapor, chlorine dioxide gas is generated. The chlorine dioxide gas can then be absorbed by water to produce a chlorine dioxide solution. As discussed herein below, the reaction can be initiated when the chemical precursors are exposed to water or water vapor, when a small amount of water is packaged with the chemical precursors, and/or when water is injected into the chemical precursors.

The embodiments above show the chemical precursors contained within the cartridge. However, other embodiments are possible. In some embodiments, cartridge 5 comprises at least one sachet. Particularly, the sachet can house the chemical precursors needed to generate a sterilizing solution. FIGS. 2a and 2b illustrate one embodiment of sachet 400. Specifically, sachet 400 is sealed on edges 401 using heat seal, adhesive, or any other method known in the art to enclose the sachet contents within its interior. Sachet 400 further comprises outer package 405, inner envelope 410, and chemical precursors 415.

Outer package 405 is a hermetically sealed non-permeable package that houses inner envelope 410 within outer cavity 412. One of ordinary skill would understand that outer package 405 can be constructed from any of a wide variety of non-permeable materials, including (but not limited to), aluminum foil, plastic foil, treated paper, and the like. Alternatively, outer package 405 can be a formed or molded part constructed from plastic and/or similar materials. One of ordinary skill in the art would also understand that outer package 405 can take any of a wide variety of shapes, such as rectangular, square, round, and the like and is not limited to the shape set forth in the Figures. In some embodiments, outer package 405 can comprise indicator 420, which can include a bar code, RFID, or other identifying means that can be read by the apparatus.

As illustrated in FIG. 2b, inner envelope 410 houses chemical precursors 415. Inner envelope 410 is constructed from a selectively permeable material that allows water vapor to pass therethrough and contact chemical precursors 415 housed within inner cavity 411. In addition, inner envelope 410 allows generated chlorine dioxide gas to pass therethrough and exit the envelope. In some embodiments, the inner envelope is impermeable to liquid water. Inner envelope 410 can be constructed from any of a wide variety of selectively permeable materials known in the art, including (but not limited to) polypropylene, polyethylene, and polysulfone membrane. For example, in some embodiments, inner envelope 410 can be constructed from polypropylene membrane filter material PP045 (available from Sterlitech Corporation, Kent, Wash., United States of America).

Chemical precursors are ultimately combined with an initiator (which in some embodiments can be water vapor) to generate chlorine dioxide gas. In some embodiments, the chemical precursors can be sodium chlorite and citric acid. One of ordinary skill in the art would recognize that the presently disclosed subject matter is not limited to the generation of chlorine dioxide by sodium chlorite and citric acid. Rather, the disclosed system includes the wide variety of metal chlorites and acids that can be used to generate chlorine dioxide. Chemical precursors 415 can be in tablet, capsule, or powder form and can be mixed or separated. The absolute and relative quantities of chemical precursors 415 can be selected based on the quantity and rate of chlorine dioxide production desired. Such routine experimentation is known to those of ordinary skill in the art.

In some embodiments, at least one additive can also be housed within inner cavity 411 of inner envelope 410. Such additives can include (but are not limited to) desiccants, scents, surfactants, colorants, gelling agents, and the like and can be in pellet, powder, film, paper or other forms. FIG. 2c illustrates one embodiment of sachet 400 wherein desiccant 425 is in paper form and is positioned within inner cavity 411 of inner envelope 410 to separate chemical precursors 415. One of ordinary skill in the art would recognize that any additive can be substituted for desiccant 425 in the above description.

Figure 2D:
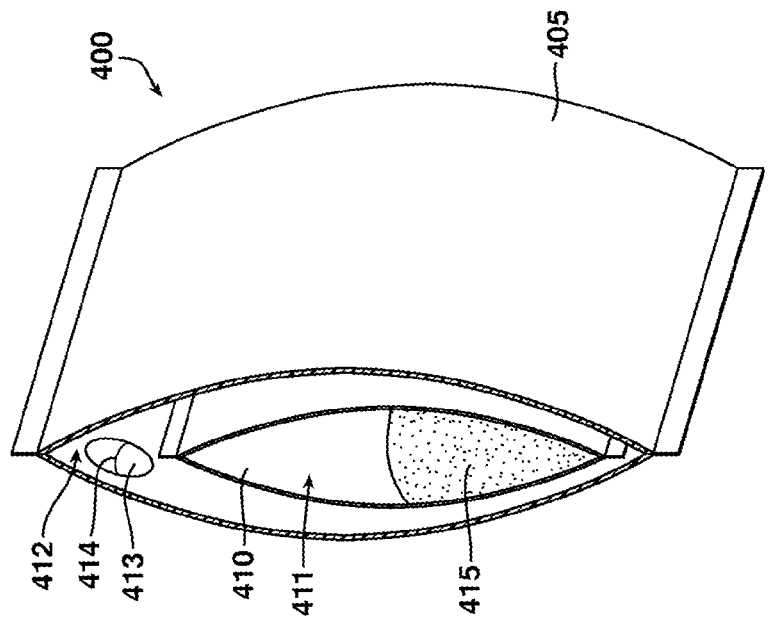
Figure 2C:
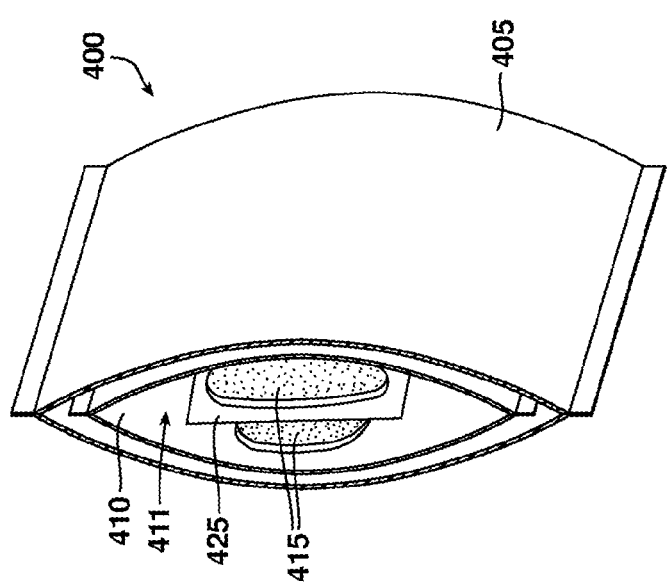

FIG. 2d illustrates one embodiment of sachet 400 wherein outer cavity 412 comprises inner envelope 410 housing chemical precursors 415, as well as frangible pouch 414 comprising water 413. Frangible pouch can be any container comprising at least one frangible seal, as would be apparent to those of ordinary skill in the art. In use, a user or the apparatus disclosed herein can rupture the frangible seal of frangible pouch 414, thereby releasing the water housed therein within outer cavity 412. As a result, water vapor can pass through inner envelope 410 to initiate the reaction between chemical precursors 415.

The chemical reaction used to generate chlorine dioxide gas can be contained within a reaction chamber to control the passage of water and absorption of chlorine dioxide. One of ordinary skill in the art would recognize that the presently disclosed subject matter is not limited to applications wherein chlorine dioxide is generated. Rather, the disclosed system can include other sanitizers, such as iodine-based or bromine-based solutions, as well as other forms of chlorine, if the correct reactants are used. Such sanitizers are well known to those of ordinary skill in the art.

Figure 3A:
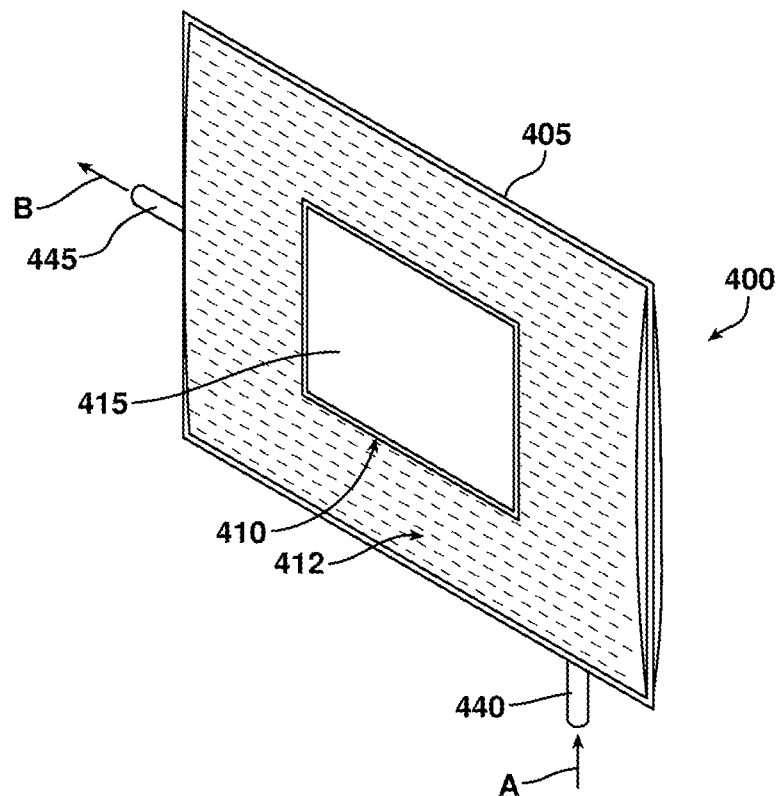
FIG. 3a is one embodiment of a sachet that can be used with the presently disclosed subject matter.

To this end, in some embodiments, outer package 405 can function as the reaction chamber. For example, FIG. 3a illustrates one embodiment wherein sachet 400 is used as the reaction chamber. Sachet 400 comprises entry port 440 and exit port 445 that are aligned with an attaching means, piercing cannula, or the like that makes a hydraulic connection. In use, as illustrated by arrow A, water passes through outer package 405 at entry port 440 into outer cavity 412 at a predetermined rate. As the water circulates in the area between the outer package and the inner envelope, water vapor passes through the selectively permeable membrane of the inner envelope to contact chemical precursors 415. As a result, chlorine dioxide gas is generated and passes through the selectively permeable membrane of the inner envelope to outer cavity 412 and is absorbed by the water as it circulates. The water then exits outer cavity 412 as chlorine dioxide solution via exit port 445, as depicted by Arrow B. Entry and exit ports 440, 445 can be constructed using any means known in the art, including (but not limited to) needle puncture directly in outer package 405. Alternatively or in addition, in some embodiments, entry and exit ports 440, 445 can be valves (such as simple diaphragms or duckbills) that mate with the apparatus, sections of self-sealing material (such as the material used in medical syringe bottles), or other systems known in the art.

Figure 3B:
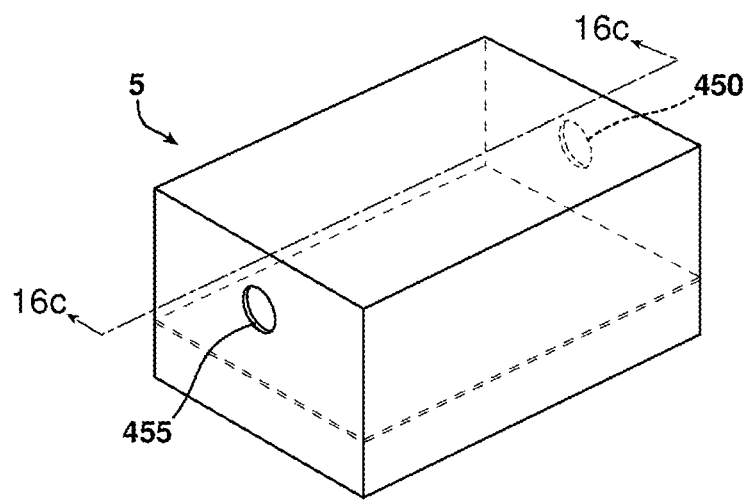
FIG. 3b is a perspective view of one embodiment of a cartridge that can be used with the presently disclosed subject matter.
Figure 3C:
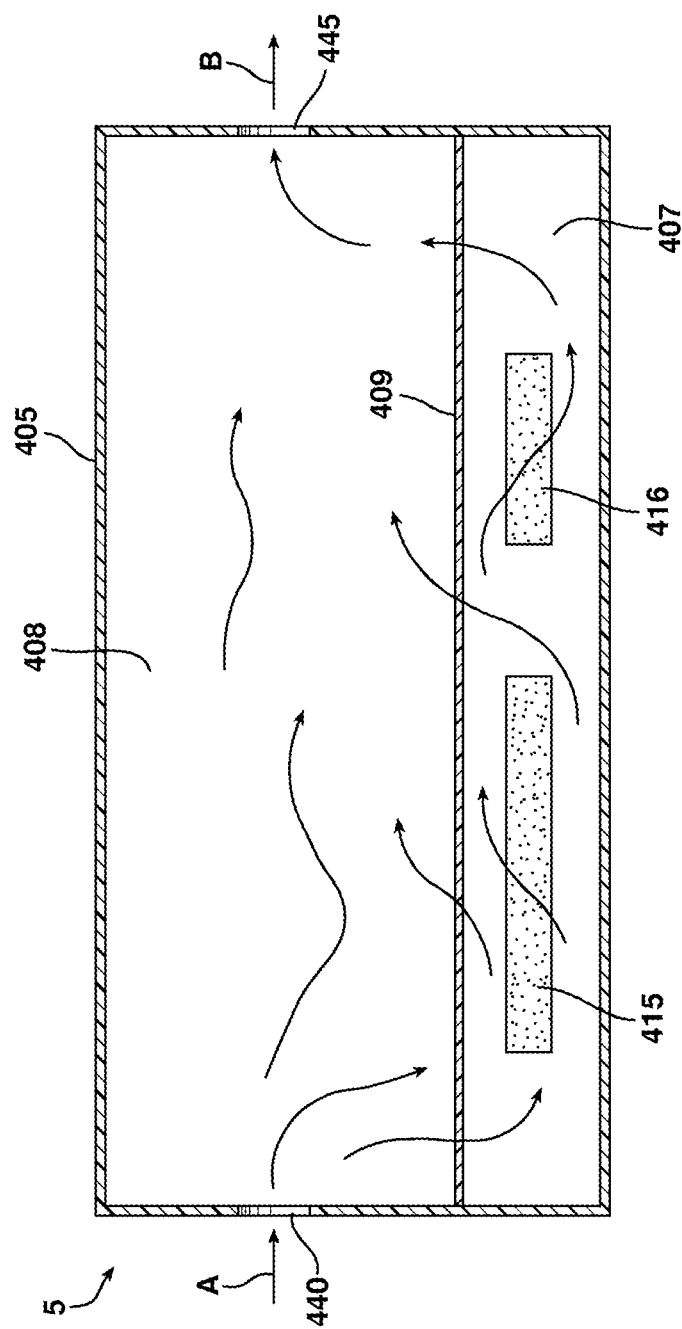
FIG. 3c illustrates one embodiment of a cartridge that can be used in accordance with the presently disclosed subject matter.

FIGS. 3b and 3c illustrate an alternate embodiment wherein outer package 405 is configured as a formed or molded part. In such embodiments, the interior of outer package 405 is divided into upper section 408 and lower section 407 by selectively permeable membrane 409. Selectively permeable membrane 409 can be constructed from any selectively permeable material that allows water vapor and chlorine dioxide gas to pass therethrough. For example, in some embodiments, selectively permeable membrane 409 can be constructed from polypropylene membrane. In some embodiments, selectively permeable membrane 409 is impermeable to liquid water.

In some embodiments, chemical precursors 415 (and optionally additives 416) are housed within lower section 407. In such embodiments, upper section 408 comprises entry and exit ports 440, 445. However, one of ordinary skill in the art would appreciate that in some embodiments, upper section 408 can house the chemical precursors and lower section 407 can house the entry and exit ports. In use, water enters upper section 408 through entry port 440, as depicted by Arrow A. Water then passes through the upper section and exits at exit port 445, as illustrated by Arrow B. In the process, water vapor passes from upper section 408 through selectively permeable membrane 409 into lower section 407 to contact chemical precursors 415. As a result, chlorine dioxide gas is generated in lower section 407 and passes through selectively permeable membrane 409 to upper section 408 and is absorbed by the water passing from entry port 440 to exit port 445. Thus, water exits the unit as chlorine dioxide solution.

In some embodiments, water can be directly injected into lower section 407 by a user or by the apparatus. In these embodiments, water and/or water vapor contact the chemical precursors and chlorine dioxide gas is generated. The chlorine dioxide gas then passes through selectively permeable membrane 409 into upper section 408 and is absorbed by water to produce a chlorine dioxide solution, as described above with regard to FIG. 3c.

Figure 4A:
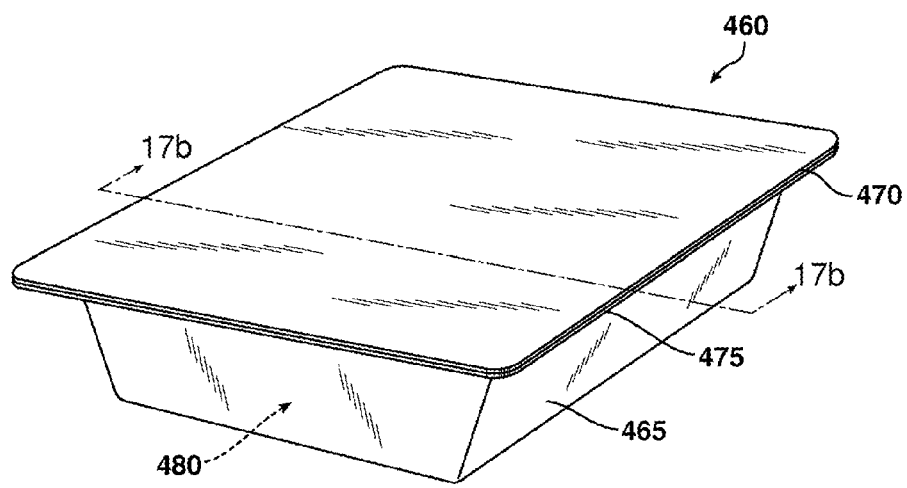
FIG. 4a is a perspective view of one embodiment of a blister pack sachet that can be used in accordance with the presently disclosed subject matter.
Figure 4B:
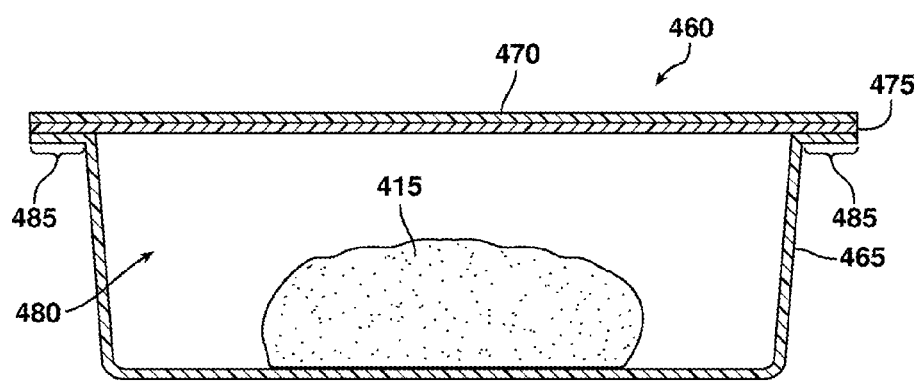

In some embodiments, sachet 400 can be a blister pack sachet. Particularly, as illustrated in FIGS. 4a and 4b, blister sachet 460 includes forming sheet 465, barrier sheet 470, and selectively permeable sheet 475 positioned in a face-to-face relationship. Forming sheet 465 is of the type conventionally used in the production of blister packs and in some embodiments can be constructed from metallic foil, polymeric material, and the like. In some embodiments, forming sheet 465 can be produced by, for example, a thermal deep drawing process. As illustrated, forming sheet 465 is provided with at least one well 480 surrounded by flange 485. Well 480 can assume any of a wide variety of shapes and is of sufficient size to house precursors 415 (and optionally one or more additives).

Selectively permeable sheet 475 is sealed to flange 485 via adhesive, heat seal, or any other method known in the art to enclose well 480. Permeable sheet 475 can be constructed from any of a wide variety of selectively permeable materials known in the art, including (but not limited to) polypropylene membrane. Selectively permeable sheet 475 allows water vapor and chlorine dioxide gas to pass therethrough, as described in more detail herein below. In some embodiments, the selectively permeable sheet is impermeable to liquid water.

Barrier sheet 470 is sealed to selectively permeable sheet 475 using any method known in the art, including adhesive and heat seal technology. One of ordinary skill would understand that barrier sheet 470 can be constructed from any of a wide variety of non-permeable materials, including (but not limited to), aluminum foil, plastic foil, and the like.

Figure 4C:
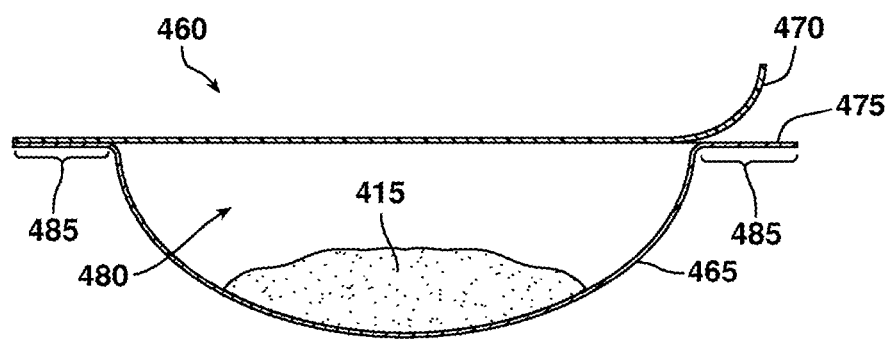
FIGS. 4c and 4d illustrate one embodiment of the blister pack sachet of FIG. 4b during use.
Figure 4D:
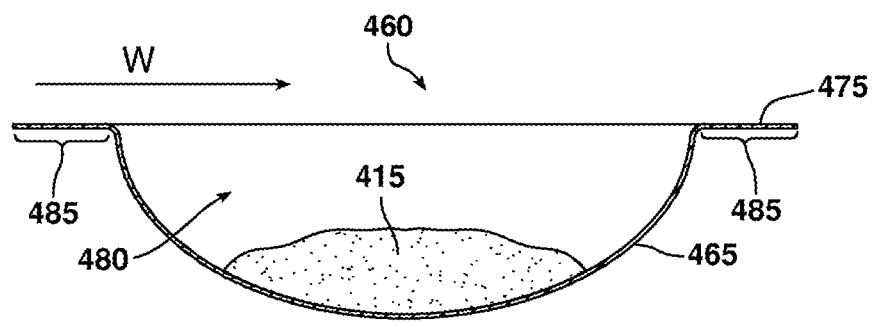

As illustrated in FIG. 4c, in use, barrier sheet 470 can be removed by a user or automatically by the apparatus to initiate production of the sterilizing solution. After barrier sheet 470 is removed, blister sachet 460 is then placed inside a chamber and the reaction is initiated by any of the methods previously disclosed such that the sachet becomes the reaction chamber (such as the method disclosed above for sachet 400). For example, as illustrated in FIG. 4d, in some embodiments supply water (represented by arrow W) can flow across the surface of permeable sheet 475, absorbing chlorine dioxide as it passes, creating the sanitizing solution.

As would be apparent to those of ordinary skill in the art, multiple blister sachets can be supplied on a roll, sheet, linear package, concentric ring, strip, or any other preformed interconnection, wherein each sachet contains the quantity of chemical precursors needed for one batch of sanitizing solution. In some embodiments, the blister sachet can have perforations that allow one sachet (sized for one batch of sanitizing solution) to be separated from the other sachets by tearing it away from the rest of the blister sachets. The individual blister sachets can be separated prior to use or can be separated prior to bulk packaging.

In this manner, multiple sachets can be loaded into the apparatus, which then indexes them into and out of the location at which they are reacted. In these embodiments, the operator does not need to change the cartridge for each batch of solution, allowing the apparatus to run in a more automatic manner. Reacted sachets thus can remain in a protected location within the apparatus while the remaining sachets are used, ensuring that the chemicals are completely reacted, and the sachet is dry before the operator handles the pack.

In some embodiments, blister sachet 460 can be divided into two compartments by a selectively permeable membrane. The selectively permeable membrane can be constructed from any of a wide variety of selectively permeable materials known in the art, including (but not limited to) polypropylene membrane. The selectively permeable membrane allows water vapor and chlorine dioxide gas to pass therethrough. In some embodiments, the selectively permeable membrane does not allow water to pass therethrough.

Figure 5A:
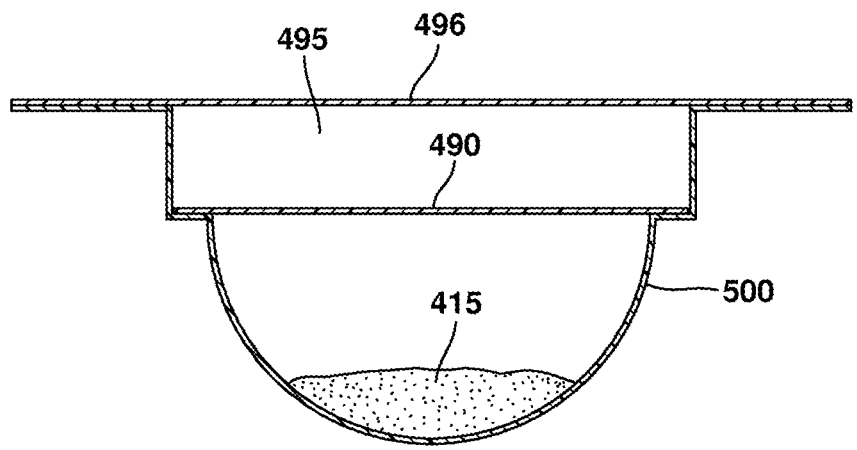
FIG. 5a illustrates one embodiment of a two compartment blister pack sachet in accordance with the presently disclosed subject matter.

FIG. 5a illustrates one embodiment of a two compartment blister sachet that can be used with the presently disclosed subject matter. Particularly, selectively permeable membrane 490 divides well 480 into upper compartment 495 and lower compartment 500. Upper compartment 495 can be a water supply compartment and lower compartment 500 can house chemical precursors 415 (and optionally additives). One of ordinary skill in the art would recognize that the presently disclosed subject matter also includes embodiments wherein the chemical precursors are housed in upper compartment 495 and the water supply compartment is the lower compartment. The two compartment blister sachet can be a formed blister, as illustrated in the embodiment of FIG. 4 with a more complex shape that leaves a flat section between the upper and lower compartments. Membrane 490 can then be adhered to the flat section by any suitable method known in the art, including adhesive and/or heat sealing.

Figure 5B:
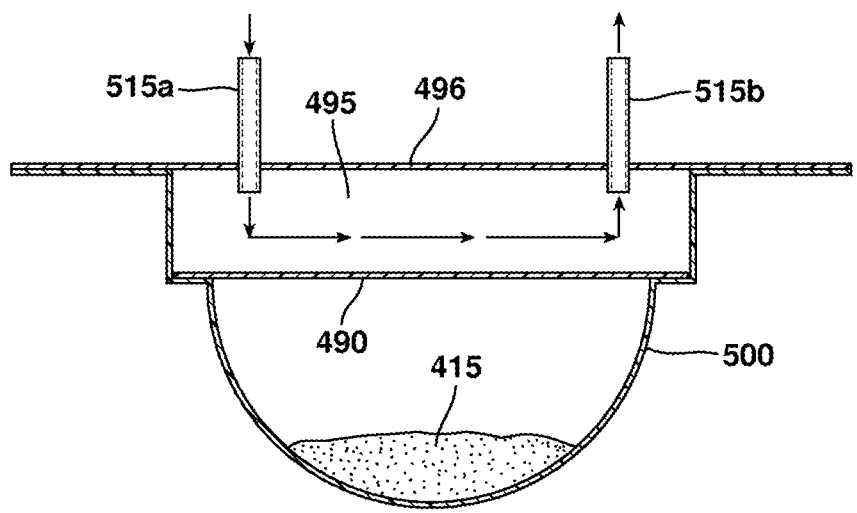
FIG. 5b illustrates one embodiment of the sachet of FIG. 5a during use.

In use, water is passed through upper compartment 495 using any of a wide variety of methods known in the art. For example, as illustrated in FIG. 5b, in some embodiments, upper compartment 495 can be pierced using a sharp instrument (such as a cannula 515) or similar device. The cannula will deposit water into upper compartment 495 via input cannula 515a and direct water out of the sachet as chlorine dioxide solution via exit cannula 515b, as illustrated by the arrows. Particularly, water will flow from input cannula 515a across selectively permeable membrane 490. As a result, water vapor passes from upper compartment 495, through selectively permeable membrane 490 to contact chemical precursors 415 in lower compartment 500, thereby generating chlorine dioxide gas. The generated gas will pass through selectively permeable membrane 490 into upper compartment 495 and will be absorbed by the water flowing through the upper compartment. As a result, water leaving the sachet via exit cannula 515b will be in the form of chorine dioxide solution.

Figure 6A:
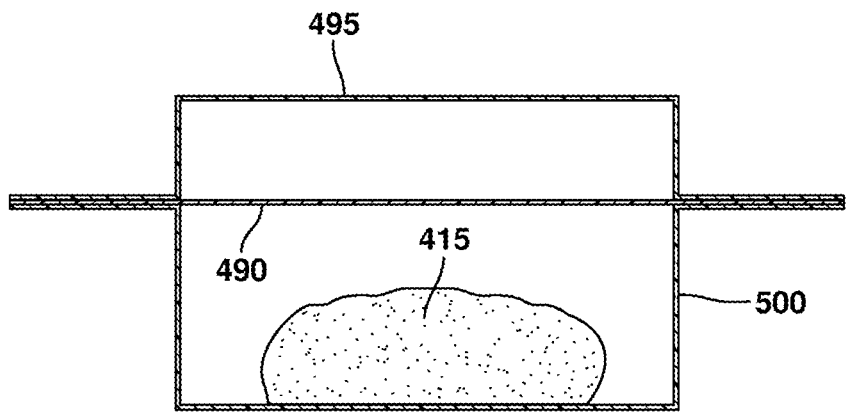
FIG. 6a illustrates one embodiment of a two compartment blister pack sachet in accordance with the presently disclosed subject matter.

In some embodiments, the two compartment blister sachet can be configured as set forth in FIG. 6a. Specifically, in some embodiments, the sachet can comprise upper and lower wells 495, 500. The blister sachet of FIG. 6a can be constructed by forming the upper and lower wells as separate blisters that are sealed together once the reactants and membrane are inserted. Alternatively, the blister can be of a clamshell design such that once the reactants and membrane are placed into one side, the clamshell is folded over and sealed using adhesive and/or heat sealing technology known in the art.

As illustrated in FIG. 6a, selectively permeable membrane 490 separates upper and lower wells 495, 500. Selectively permeable membrane 490 can be constructed from any of a wide variety of selectively permeable materials known in the art. For example, in some embodiments, the selectively permeable membrane can allow water vapor and chlorine dioxide gas to pass therethrough. In some embodiments, the selectively permeable membrane can be constructed from polypropylene membrane.

Figure 6B:
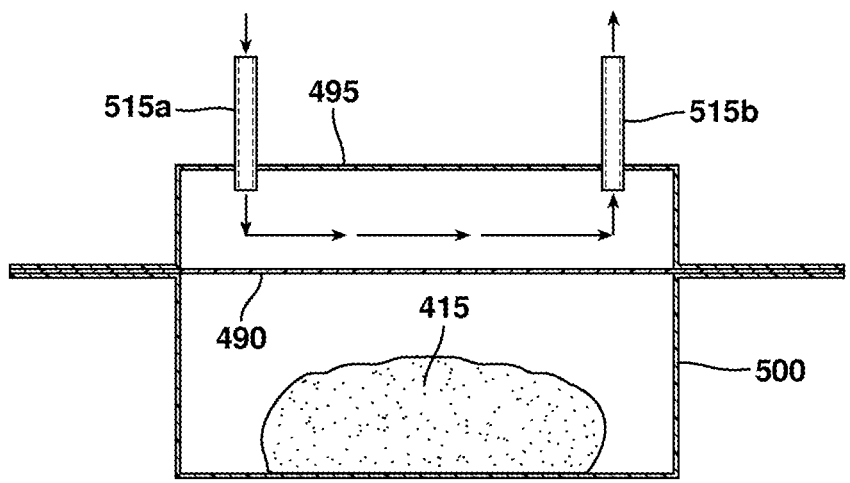
FIG. 6b illustrates one embodiment of the sachet of FIG. 6a during use.

In use, water enters upper well 495 using any of a wide variety of methods known in the art. For example, in some embodiments, upper well 495 can be pierced using a sharp instrument (such as a cannula 515) or similar device. As illustrated in FIG. 6b, the cannula will deposit water into upper well 495 via input cannula 515a. The water will flow from input cannula 515a across membrane 490 and exit upper well 495 via exit cannula 515b. As a result, water vapor passes through membrane 490 and enters lower well 500 to contact chemical precursors 415, thereby generating chlorine dioxide gas. The generated gas will pass from lower well 500, through membrane 490 and into upper well 495 and will be absorbed by the water. Thus, water that leaves the sachet via exit cannula 515b will be in the form of chlorine dioxide solution.

In another embodiment, shown in FIGS. 7a-b, the cartridge 300 may by rigid, constructed from materials such as plastics such as polypropylene. FIG. 7a shows the back portion 301 of the cartridge 300. In some embodiments, back portion 301 may include a handle 304, which can be used to install and remove the cartridge 300 from the apparatus (not shown). Back portion 301 may also include two openings 305, through which water or water vapor may enter the cartridge 300. In some embodiments, a tube from the apparatus is pressed into the openings 305, which creating a path through the cartridge 300. FIG. 7b shows the cartridge 300 assembled. A front portion 302 is affixed to the back portion 301, so as to create a space 306 therebetween. This space 306 may house the chemical precursors, and may serve as the reaction chamber.

In this embodiment, the cartridge comprises two pieces 301, 302, which may be affixed to each other using any fastening mechanism, including screws, glue, snap-fit, or heat bonding. In one embodiment, screws 307 pass through openings 308 in the back portion 301 and attach to the front portion 302, as shown in FIG. 7b.

Figure 8B:
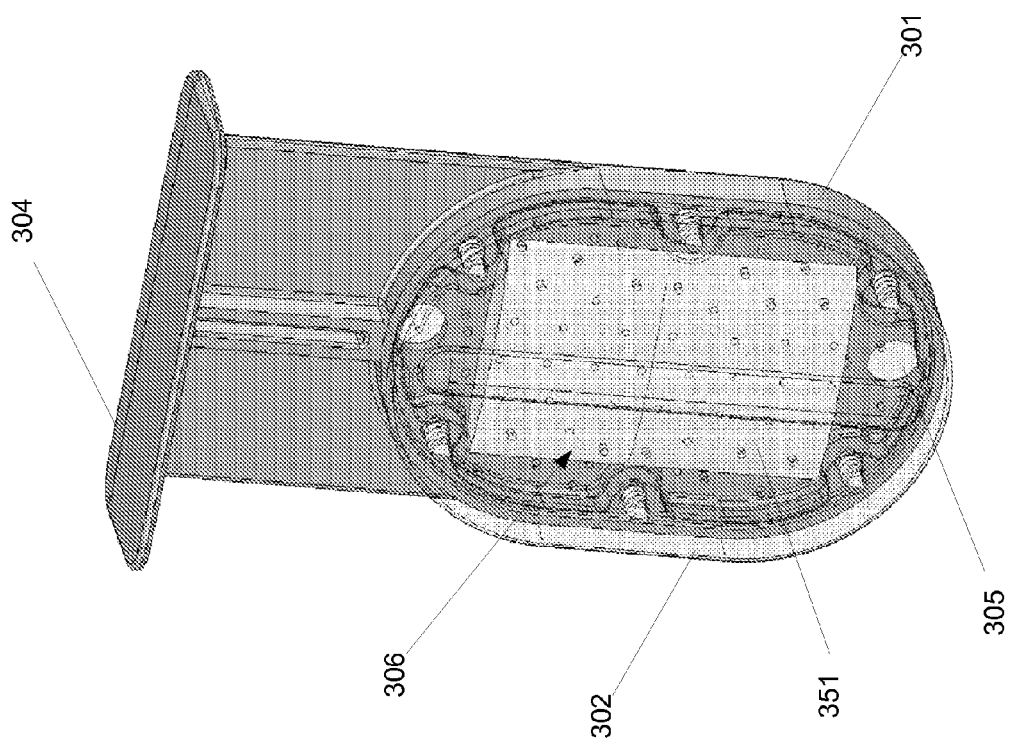
FIG. 8b shows the cartridge of FIG. 7b with a sachet having two compartments placed within the cartridge.
Figure 8A:
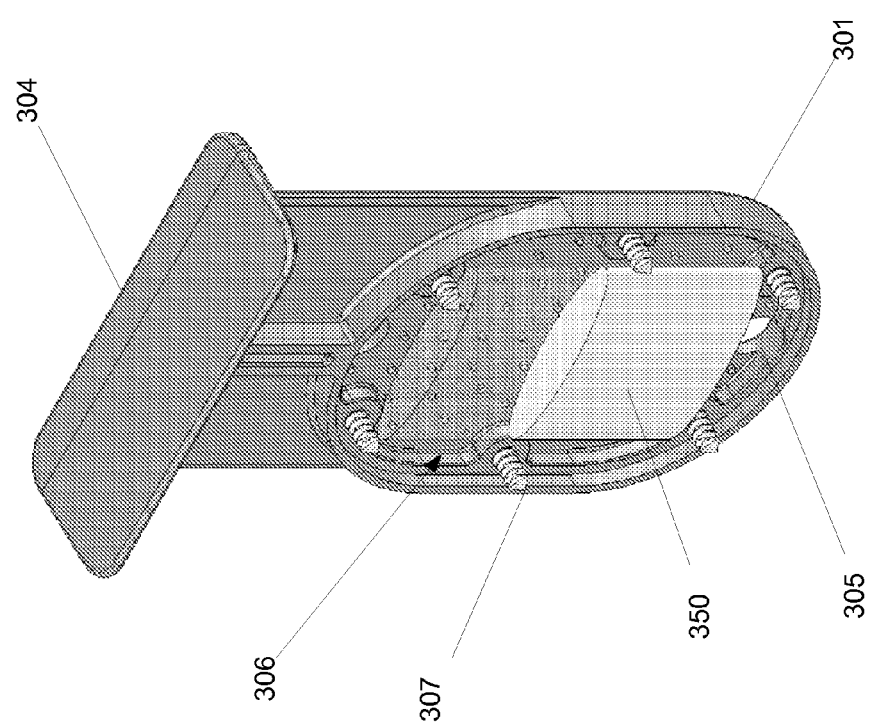
FIG. 8a shows the cartridge of FIG. 7b with a sachet having one compartment placed within the cartridge.

As shown in FIG. 8a, an inner envelope 350 may be placed within space 306. In this Figure, front portion 302 has been removed for clarity. The inner envelope 350 is sized to fit within the space 306, without contacting the fasteners 307. In some embodiments, the inner envelope 350 is sized to allow tubes or other devices to be inserted in openings 305 without contacting the inner envelope 350.

In FIG. 8a, the inner envelope 350 has a single compartment where all chemical precursors are stored. In FIG. 8b, an inner envelope 351 having two compartments is shown. This configuration has two openings 305, which allow water, or another fluid to enter the cartridge 300, and specifically the space 360, through one opening and exit through the second opening. Additional openings 305 can also be added if desired, as long as there is an ingress and egress for fluid passing through the cartridge 300.

The inner envelope comprises a selectively permeable membrane, thereby allowing water that enters through the opening 305 to pass around the envelope, and further allowing water vapor to pass through the selectively permeable envelope to initiate the reaction of the chemical precursors. In some embodiments, after the cartridge 300 has been used, it is discarded. In other embodiments, the depleted inner envelope 350 is removed from the cartridge 300 ad replaced with a fresh inner envelope 350.

In some embodiments, heat can be used as a catalyst to increase the rate of chlorine dioxide production. Particularly, the water that flows around the inner envelope 350 can be heated, or the cartridge 300 itself can be heated with a hot plate or other surface heater. In some embodiments, the heater can be included as part of the cartridge, or as an integral part of the apparatus. Alternatively or in addition, an exothermic chemical reaction that produces heat can be used, such as (but not limited to) Portland cement, or similar chemicals that can be intermixed to produce heat.

The generating apparatus disclosed herein is an automatic or semi-automatic device into which cartridge 300 is inserted. The apparatus is attached to a source of water controlled through the cartridge to create the sanitizing solution. The apparatus then stores and dispenses the prepared sanitizing solution.

Figure 9A:
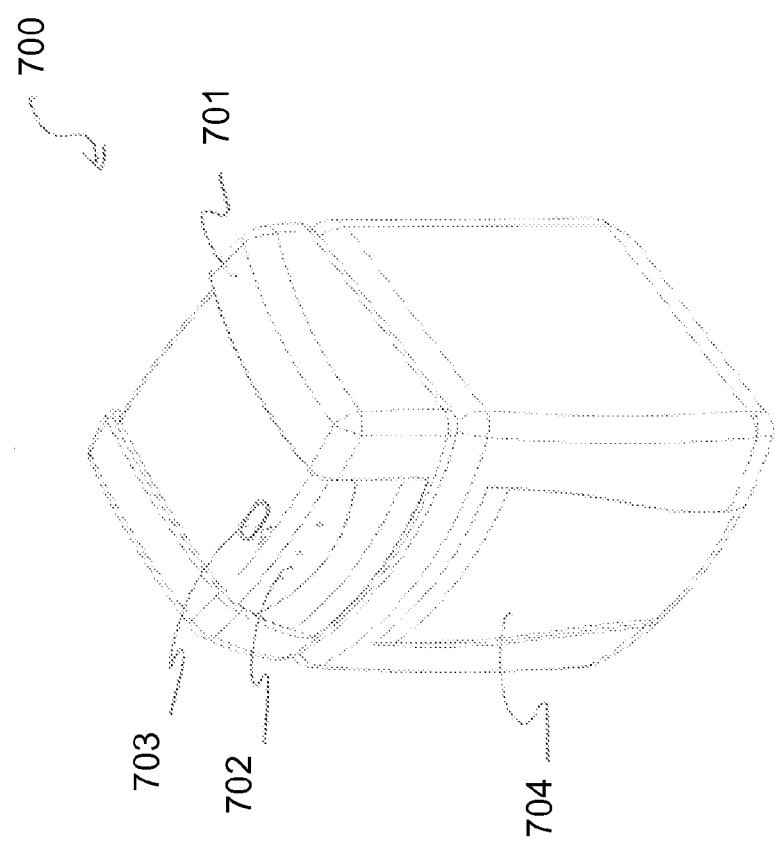
FIGS. 9a-c are one embodiment of a system that can be used to chemically produce a cleaning and/or sanitizing solution.

FIG. 9a shows an isometric view of one embodiment of an apparatus 700 that can be used with the current invention. The upper portion 701 contains the electronics, controls, plumbing, etc. necessary to operate the apparatus. On the front panel are indicators, such as LED lights 702 or an electronic display (not shown), which indicate the operational status of the apparatus 700. A receptacle 703 shown here on the top of the apparatus 700, provides access to a reaction vault and accepts a cartridge containing the chemical precursors. The lower portion 704 of the apparatus contains a reservoir for holding prepared solution as well as one or more pumps and associated plumbing used to distribute the solution from the reservoir to a sink, misting system or other use as desired. The lower section may also contain liquid level sensors and other components.

Figure 9C:
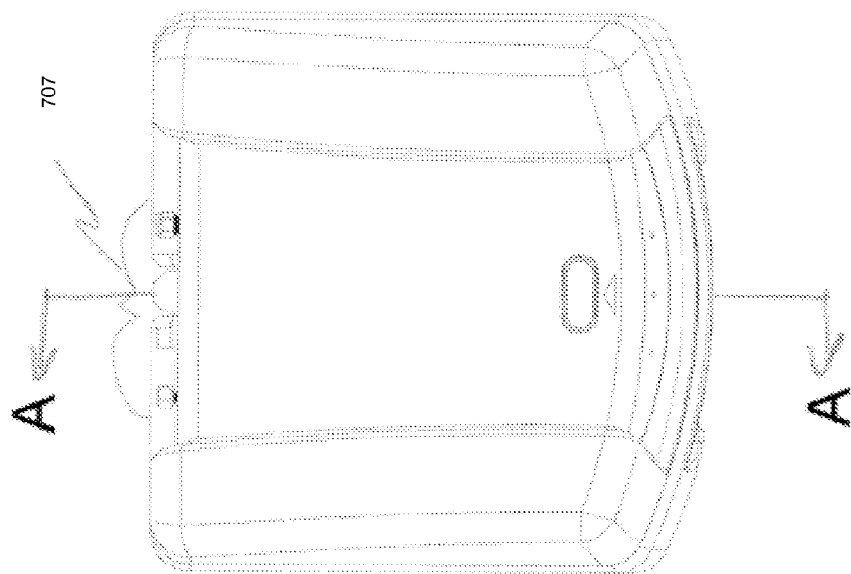
Figure 9B:
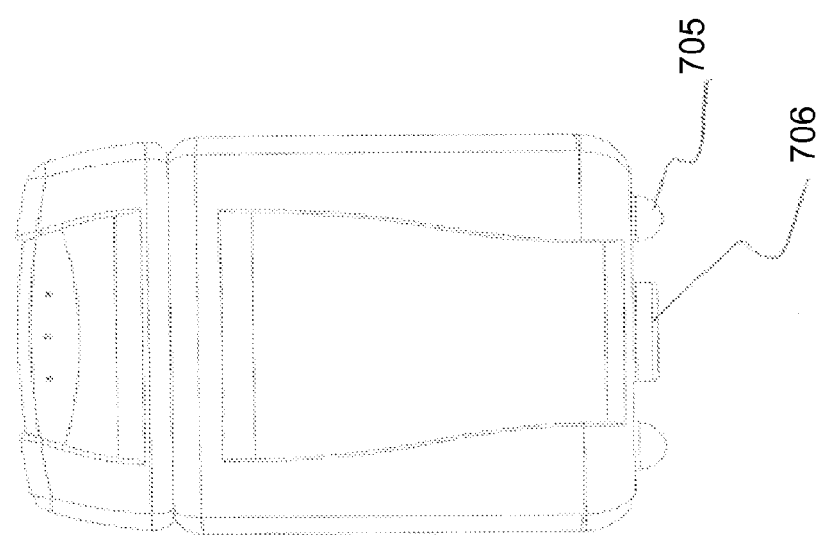

FIGS. 9b and 9c show a front elevation view and top plan view respectively. On the bottom are feet 705 that can be stationary, rollers, casters, or a combination. The lowered portion 706 is a provision for an internal sump that allows the pump to remove as much solution as possible. On the rear are the connections 707 for water and electric inputs and solution outputs. The shapes and locations shown in these figures are for illustration purposes. Embodiments with alternate configurations determined by preference and practice are within the scope of the current invention.

Figure 10B:
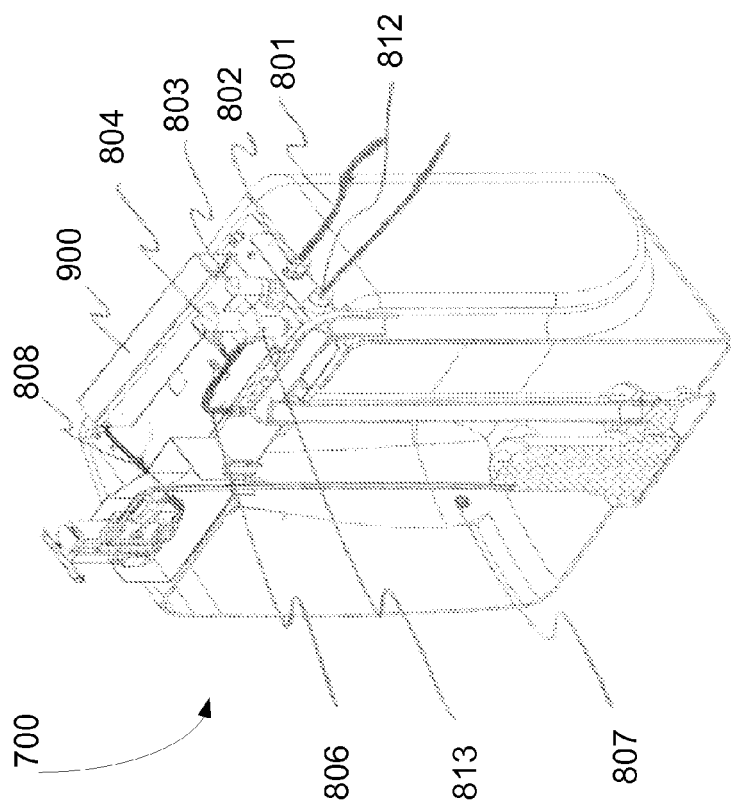
Figure 10A:
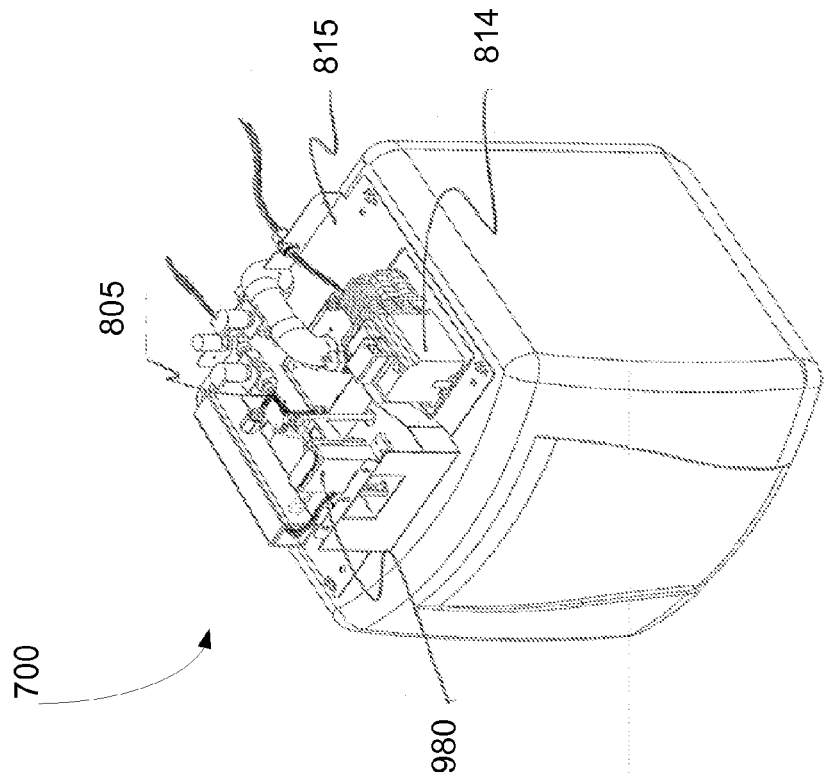
FIG. 10a is the embodiment of FIG. 9a with the cover removed to expose the internal components.

FIG. 10a is an isometric view of the apparatus with the upper section cover removed. FIG. 10b is an isometric view, with the upper cover removed, through section A-A of FIG. 9c. FIG. 10c is an elevation view through section A-A of FIG. 9c, also with the upper cover removed.

Fresh water is supplied to the apparatus 700. The water can be supplied from any available source, but will most commonly be in the form of tap water from a municipal water supply. If it is determined necessary, the water can be filtered or otherwise treated, by the use of filters, water softeners and/or other devices. Although water is preferred, other fluids are also within the scope of the disclosed subject matter. A pressure regulator can be employed if constant input pressure is deemed necessary. These devices can be either external to the apparatus 700 or can be built into the apparatus 700 (not shown). The fresh water supply may enter the apparatus 700 through tubing 801 into a connector 802, as shown in FIG. 10b. The connector 802, as well as other plumbing components and tubing can be any suitable type, and are commonly available from commercial sources. A pressure transducer 803 monitors the pressure of the fresh water supply. Such transducers are common in the art, for example, the TDH30 series pressure transducer from Transducers Direct of Cincinnati, Ohio. The flow of water into the system is controlled by an electric solenoid valve 804, which is preferably an on/off, normally closed device such as model P462 manufactured by Dema Engineering of St. Louis, Mo. However, any suitable solenoid valve or other flow control device can be used, and can be an on/off or variable flow design. The flow of fresh water is then split into two streams by a tee 805 (see FIG. 10a). A major portion of the water passes through a tube 806 and enters the reservoir 807. A minor portion of the flow enters a heating chamber 900, where the water is heated. The heated water exits the heater, passes through a tube 808 and into the reaction vault 980. Inside the vault 980, the chemical reaction occurs that produces chlorine dioxide gas, which is absorbed into the heated water. This chlorine dioxide solution then exits the vault 980 and enters the reservoir 807 through a tube 809 (see FIG. 10c), where it joins and mixes with the fresh water, creating a solution of the correct concentration. In some embodiments, this tube 809 extends to a location near the bottom of the reservoir 807 so that the solution is delivered into the fresh water, which aids in mixing.

In one embodiment, to control the quantity of solution inside the reservoir 807, one or more liquid level indicators (not shown) are used. Since the reservoir 807 is a fixed volume, if the fluid level inside is known, the quantity of available fluid can be calculated. It may preferable to know at least two fluid levels inside the reservoir 807. It is important to know when the fluid level reaches its desired fill volume, as this information is used to determine the end of the solution-making cycle. In some embodiments, a reserve capacity is included for misting and other applications. A lower level sensor can signal when this fluid level is reached. In one embodiment, the fill capacity is 30 gallons, and the reserve capacity is 5 gallons. In some embodiments, it may be preferred to include a sensor to determine when the reservoir 807 is empty. Liquid level sensing is common in the art and may be accomplished in a variety of ways. One example is the use of a multi-level float switch, such as model 96087 manufactured by Innovative Components of Connecticut. Alternately, other devices such as ultrasonic or capacitive sensors may be used. In other embodiments, a volumetric flow meter can be used to determine the amount of fluid in the reservoir.

Solution can be dispensed from the apparatus 700 in two ways. Large volumes of solution may be pumped into a soaking sink or similar large vessel by an on-board pump 810 that may be located in a sump at the bottom of the reservoir 807. This can be any suitable pump, such as Model A53S from Rule Industries of Gloucester, Mass. This pump 810 may fill a standard wash sink in about one minute. Solution from the pump exits the apparatus through a tube 811, which is generally connected to the sink via a hose. The liquid level indicator described above uses its lower fluid level indicator to signal when the correct amount of solution to fill the sink has been pumped out. The controller then stops the pump 810. In one embodiment, this is 25 gallons, which is the difference between the full and reserve indications.

Another method by which the solution may be dispensed is through a connector 812 (see FIG. 10b), and can be used in some embodiments for misting produce and other food products. Misting systems located downstream of this apparatus are common in the art and will not be described in detail here. The ability to access the misting solution is controlled by a solenoid valve 813. This can be used to prohibit the dispensing of solution when desired, such as during a solution production cycle. A tube (not shown) connects to the inlet side of the solenoid valve and extends to the bottom of the reservoir to allow solution to be available in reserve even after enough solution has been removed to fill a sink. The pumping means for the misting outlet can be part of the misting system, or alternatively, a suitable commercially available pump can be part of the apparatus of the current invention. In some embodiments, solution from this outlet can be used to fill pump spray bottles or other applications where the solution can be used.

The electronic controller 814 is programmed to control the operation of the apparatus, including solution production cycles, dispensing, safety controls, etc. The controller can be any device common in the art, including programmable logic controller (PLC), embedded computer, custom circuit board, etc. In the preferred embodiment, the controller is located in the upper section of the apparatus, along with all the sensors, switches, wiring, etc., that need not be placed within the reservoir. They can be mounted to a common base plate 815 to make a unitized control package that is isolated from the reservoir, protecting the components from liquid contact.

Figure 11:
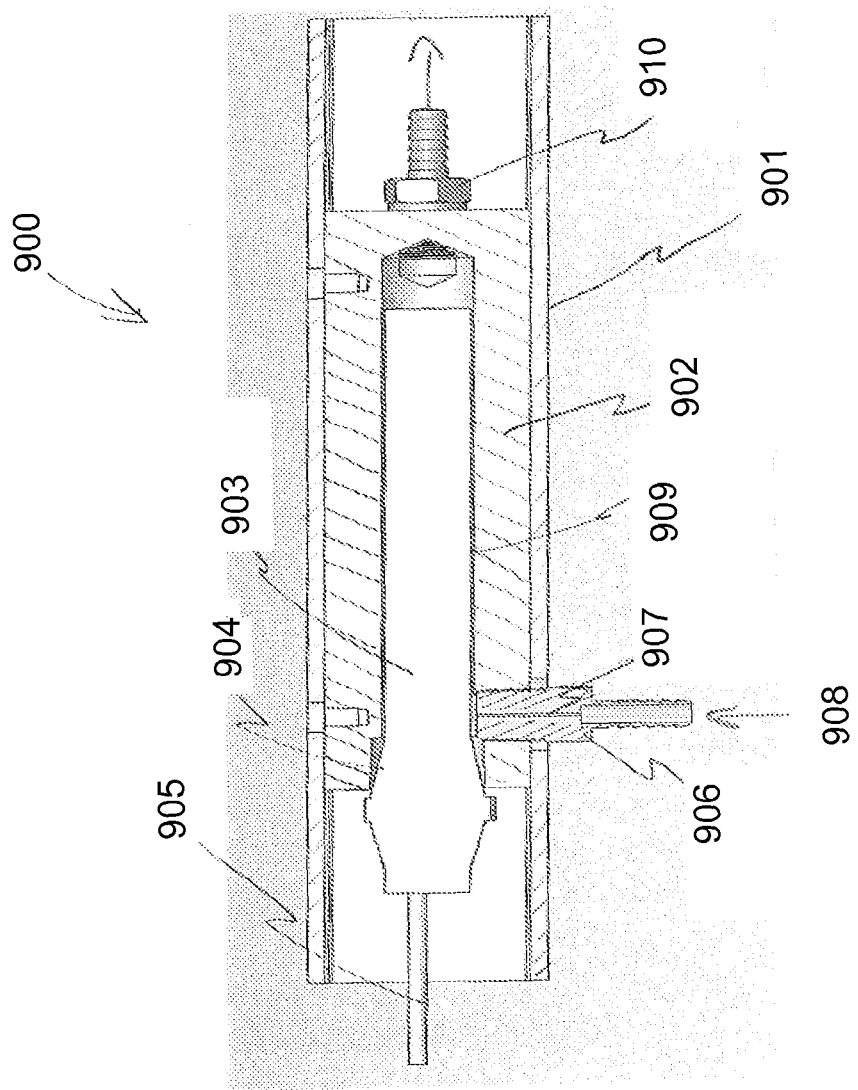
FIG. 11 is a cross-section view of a heating element that can be used in the apparatus of FIGS. 9 and 10.

FIG. 11 shows a cross-section of one embodiment of the heater assembly 900. A mounting channel 901 can be made from square steel tubing or other suitable material. The heater block 902 can be made from aluminum or any other suitable material. If a heat conduction material, such as aluminum, is used for the heater block, it may be preferable to cover the block with a heat insulating material to keep excess heat from leaving the heater assembly 900. The heating element 903 can be sized as necessary and determined by the specific design requirements. In one embodiment, the heating element may be a cartridge style immersion heater producing approximately 800 watts of heat, be ½ in diameter and 6" long, and be attached to the heater block 902 by a screw type pipe fitting 904 in order to be to be water tight. Electric power is supplied to the heating element 903 via wires 905. These heating elements 903 are commercially available, such as the EM50-6 manufactured by Hotwatt of Danvers, Mass. The inlet fitting 906 is teed into the fresh water supply as previously described. The fitting 906 may have an internal orifice 907 that limits the flow of water through the heating element 903. In one embodiment, the orifice is 0.028 inches in diameter and limits the flow to approximately 2 gallons per hour. Other types of flow restrictors known in the art may be used. One such example is the use of a small diameter capillary tube cut to length to produce the desired pressure loss. Alternatively, the flow restrictor may be located in the supply tee 805, or in a location between the tee and the heater.

In operation, the fresh water enters the inlet fitting 908 and passes through a clearance 909 between the heating element 903 and heater block 902. The specific clearance will be determined by practice, but may be on the order of 0.025 inches. As the water passes through the clearance 909, heat is transferred to it from the heating element 903. The heated water exits the heater assembly 900 through a fitting 910, and continues to the reaction vault 980. In some embodiments, a thermocouple (not shown), such as a standard type J or K, may be mounted inside the heater block 902. The thermocouple communicates with the controller 814, which cycles the power to the heating element 903 to maintain the desired temperature. Other temperature sensing devices known in the art, such as thermistors, RTDs, infrared or other devices may be used. Alternatively, an on/off temperature switch such as a bi-metallic device can be used in lieu of a sensor and controller. The control temperature is generally on the order of 110° F., but will be determined by practice. When the heater assembly 900 is installed into the apparatus 700, it may be mounted at an angle, as shown in FIG. 11, to keep any air bubbles from becoming entrapped in the heater block 902 and affecting the efficiency of the heat transfer.

Figure 12A:
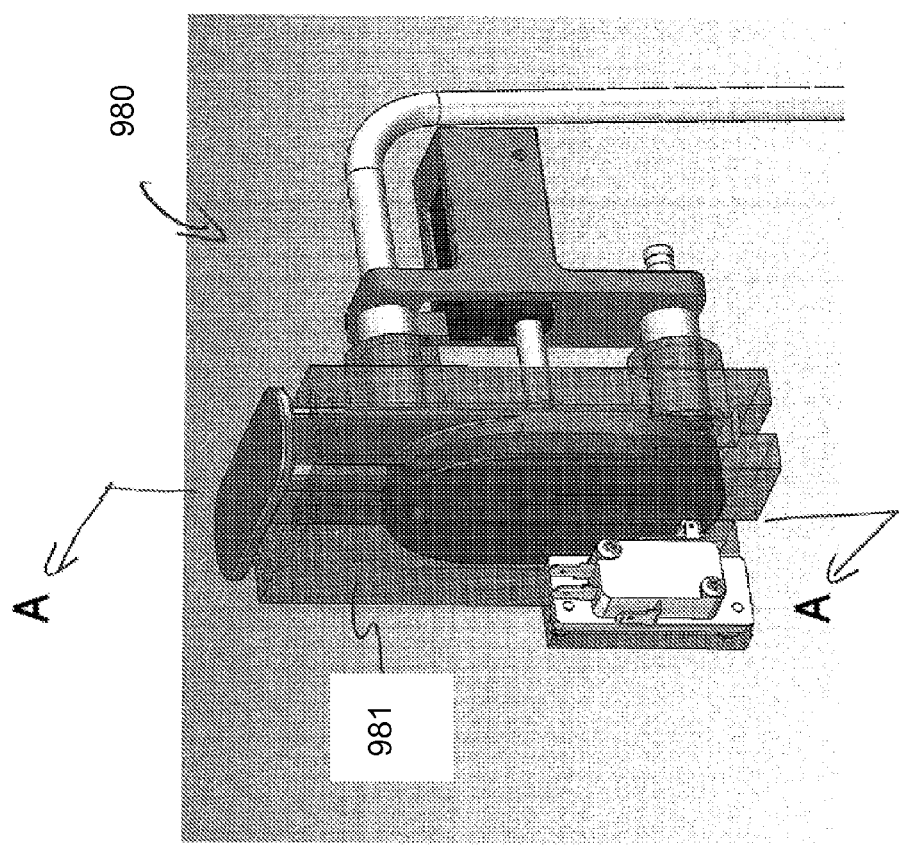
FIGS. 12a-c show the reaction chamber and its interface to the cartridge.
Figure 12B:
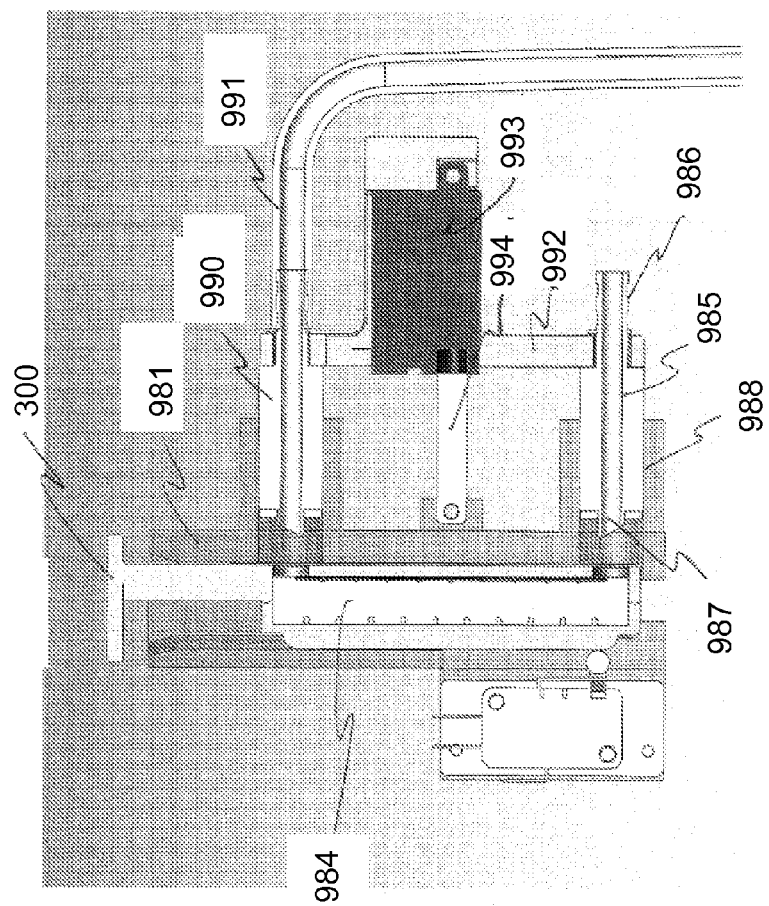
Figure 12C:
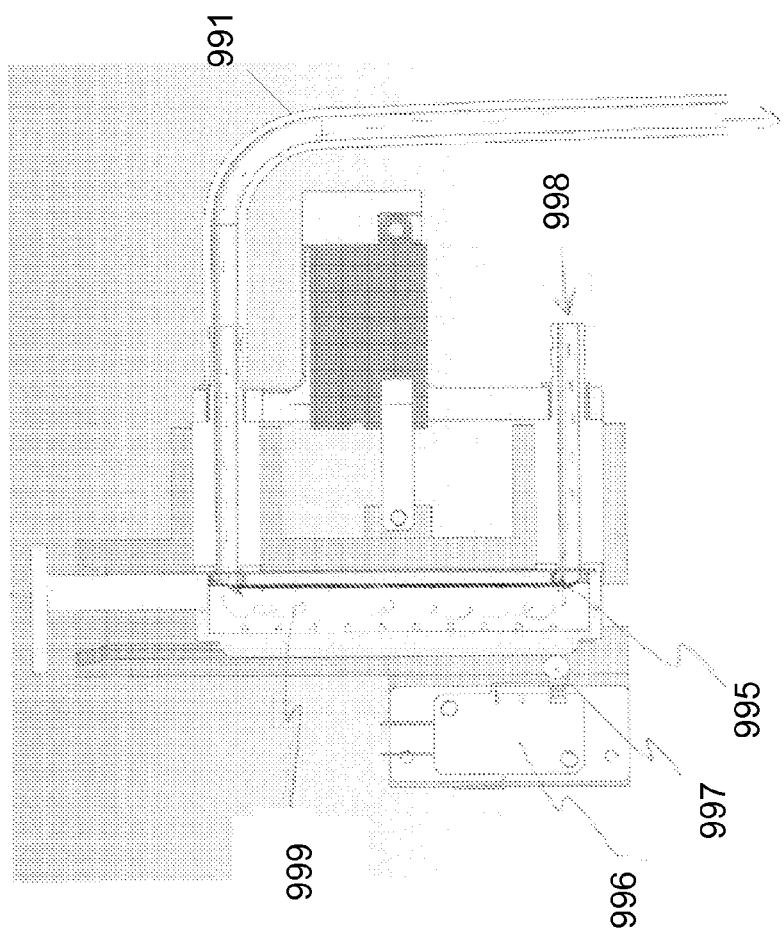

FIG. 12a shows a view of the reaction vault 980 of one embodiment. The vault body 980 is securely mounted to the base plate (shown in FIG. 10a). It is shown as transparent in this view so that the internal parts may be seen. The vault body 980 can be made from aluminum or any other suitable material. FIGS. 12b and 12c are views through section A-A of FIG. 12a. Inside the vault body is the cartridge 300. The cartridge 300 can move upward and downward, as required. In the uppermost position (not shown) the cartridge vault 984 is exposed, and a cartridge 300 can be installed. When the cartridge 300 is installed, it is in its lowermost position as shown.

Referring to FIG. 12b, in the lower portion of the vault 980 is the water inlet 985. The water inlet 985 has a tube connection 986 at one end and may comprise a cannula with a needle point 987 at the distal end. In other embodiments, the distal end may comprise a tube, which fits within an opening in the cartridge, such as opening 305 (see FIG. 7a). The outer diameter of the water inlet 985 fits within a bore 988 that is part of the vault body, in a manner that allows the inlet 985 to slide back and forth within the bore 988.

In the upper portion of the vault 980 is the water outlet 990, which, like the water inlet 985, may comprise a tube fitting on the proximal end and a needle and cannula on the distal end. In other embodiments, the distal end of the water outlet 990 may be a tube, which is inserted into an opening, such as opening 305 in the cartridge 300. The outlet 990 slides inside a bore in the vault body 980. A tube 991 is shown attached to the outlet 990. In some embodiments, the inlet 985 is placed at a lower elevation than the outlet 990. This configuration forces a volume of water to fill the cartridge 300 before any water exits through the outlet 990. This dilutes the outgoing water and also provides more water into which the chlorine dioxide gas may dissolve.

The inlet 985 and outlet 990 may be connected together by a bracket 992 which may be moved by an actuating device 993. This device 993 can be any suitable actuating device, such as electric linear actuator PQ12 manufactured by Firgelli Technologies of Victoria BC. In one embodiment, the actuator 993 is attached to the bracket 992 and moves with the water inlet 985 and water outlet 990. In this embodiment, the actuator 993 is connected to the vault body 980 by a link 994. In another embodiment, the actuator 993 is fixed to the vault body 980, and moves the bracket 992, such as by a linking member. When actuated in one direction, the assembly, which consists of the inlet 985 and outlet 990, moves forward towards the cartridge 300. In one embodiment, this causes the needles on the distal ends of the water inlet 985 and water outlet 990 to pierce the cartridge 300, providing hydraulic connections from the inlet and outlet to the cartridge 300. In other embodiments, this actuation cases the tubes to enter openings 305 in the cartridge 300, which provide fluid paths. An additional advantage of this design is that, when the water connections are engaged, they also make a mechanical connection between the apparatus and the cartridge. The tubes protrude into the cartridge, capturing it, and making it impossible to remove the cartridge until the tubes are retracted. In this manner, the cartridge cannot be removed during a reaction cycle. This prevents a partially reacted cartridge from being removed from the apparatus and producing chlorine dioxide gas outside of the apparatus. When actuated in the other direction, the needles (or tubes) are removed from the vault 980 and, therefore, the cartridge 300. The actuator 993 may include end-of-stroke limit switches to indicate that the needles (or tubes) have been fully inserted and/or removed from the vault 980. As seen in FIG. 12c, a switch 996 can be mounted to the vault body 980 so that its actuator 997 is depressed (as shown) by the cartridge 300. This switch 996 indicates that the cartridge 300 is in its lowermost position, and indicates to the controller 814 that the cartridge 300 is properly installed. These switches are common in the art, and any suitable switch may be used. Although shown with the water inlet on the lower portion of the vault 980, the configuration may be modified such that the inlet 985 is at the top portion of the vault 980 and the outlet 990 is at the lower portion.

In operation, a cartridge 300 is inserted into the cartridge vault 980. The cartridge 300 can be actuated manually, such as by pressing on the handle 304, or the apparatus may include a drive means to automatically actuate the cartridge 300. The cartridge 300 is then pushed down, causing the switch 996 to be activated, signaling to the controller 814 that the cartridge 300 is in position for use. The actuator 993 then pushes the inlet 985 and outlet 990, allowing them to enter the cartridge 300. As noted above, this may be done by piercing the cartridge 300 with needles, or the cartridge may comprise openings 305 into which tubes on the inlet 985 and outlet 990 may enter. Water that has been heated by the water heater assembly 900 enters through the inlet 998 then passes through the cartridge 300 containing the chemical precursors 999. This initiates the chemical reaction that generates chlorine dioxide. The heated water absorbs the chlorine dioxide prior to exiting through the outlet tubing 991, where it enters the reservoir 807 and mixes with the fresh water, creating a solution of the desired concentration.

Figure 13:
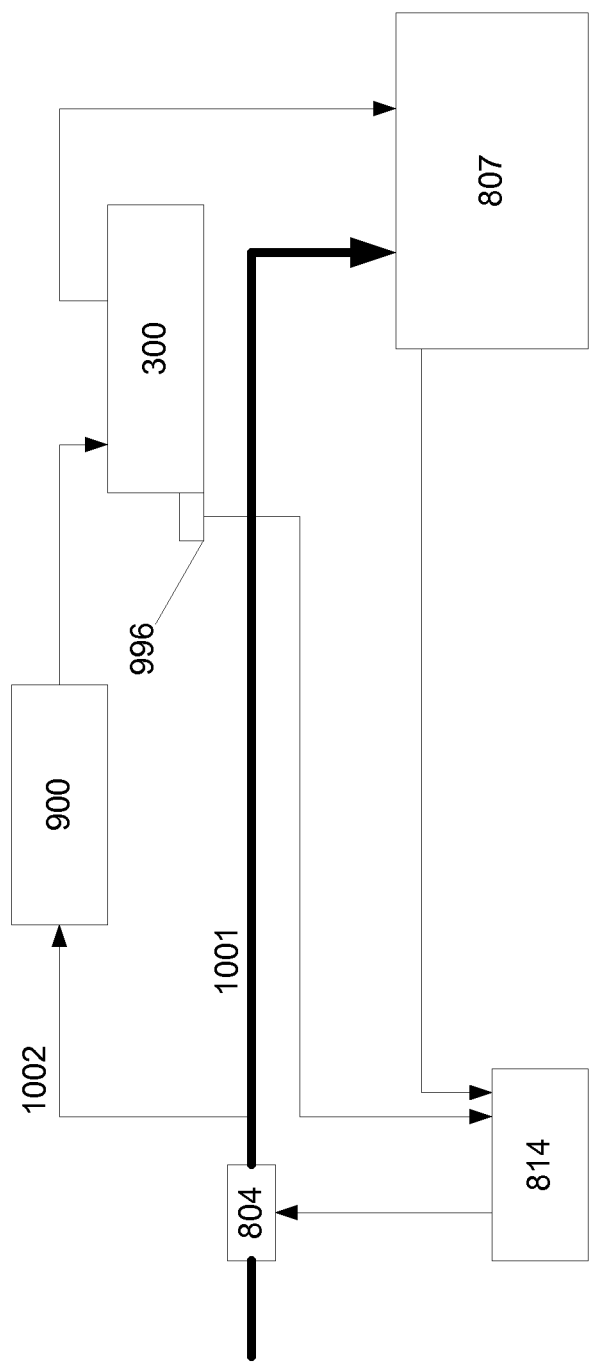
FIG. 13 shows the fluid and control paths within the apparatus according to one embodiment.

FIG. 13 shows a representative view of the fluid and control paths in the apparatus 700. Fresh water, or another fluid, enters the apparatus 700, and its flow is controlled by a regulator or valve 804. The valve 804 is controlled by controller 814. Before allowing fluid to flow, the controller 814 insures that the cartridge 300 is properly installed, such as by monitoring an output from sensor 996. The controller 814 also verifies the level of fluid currently in the reservoir 807, such as by a fluid level sensor, or using a flow meter. If the cartridge 300 is properly installed, and the reservoir level is sufficiently low, the controller will open valve 804. After passing through the valve 804, the water is divided into two flows. One flow 1001, which constitutes the majority of the volume, flows directly into the solution reservoir 807. The other, smaller flow 1002 is split off from the main flow 1001, where it passes through the heater assembly 900, which raises its temperature prior to its entering the reaction vault 980 which contains the cartridge 300 containing the chemical reactants. This produces a more efficient and complete reaction. It speeds the diffusion of chlorine dioxide gas out of the inner envelope 350, and increases the interaction of the precursor chemicals. In one embodiment, the water is heated to approximately 110° F. This temperature is high enough to always be above any ambient temperature in which the apparatus 700 will be used. This constant temperature provides consistency to the reaction, and is high enough to complete the reaction in the desired time. Highly elevated temperatures are avoided since they cause the reaction to occur too rapidly and produce a dangerous situation, allowing gas to build up inside the inner envelope faster than it can be diffused. For this reason, the temperature of the heated water is accurately controlled. Another advantage of the current invention is that only small amounts of precursor chemical is used, so any buildup of pressure due to overheating is small enough to be contained in the reaction chamber.

In one embodiment, the conduits that carry these two flows 1001, 1002 are appropriately sized so that the ratio of fluid flow in each flow is as desired. In this example, the orifice is 0.026 inches in diameter, which allows 0.03 gallons per minute to flow through the reaction vault, and 0.97 gallons per minute into the reservoir 807. In this way, at the end of the 30 minute cycle, 1 gallon has passed through the reaction vault 780, and the cartridge 300, and 29 gallons have gone directly into the reservoir 807, for a total of 30 gallons.

After heating assembly 900, the water from flow 1002 passes into and out of the cartridge 300. In another embodiment, the heating assembly 900 is not used. This eliminates the ability to control the temperature of the flow 1002, which may adversely affect the rate of reaction. However, in some embodiments, the rate of reaction may not be an important consideration. In this embodiment, water from flow 1002 directly enters the cartridge 300, as described below. As described above, the apparatus 700 interfaces with the cartridge using tubes, cannulas or needles. As the heated water passes through the cartridge 300, the water initiates the chemical reaction. The reaction produces the gas, which in this case, may be chlorine dioxide. In the case of chlorine dioxide production, metal chlorite and acid precursors react to form $ClO_2$ gas. These precursors may be inserted into an inner envelope 350 in the cartridge 300. In this case, the water is used to both initiate the reaction and to absorb the $ClO_2$ gas into solution, creating a somewhat concentrated solution, which then enters the reservoir 807 and joins with the fresh water to create a solution of the desired concentration. The total amount of chlorine dioxide produced is designed so that when mixed with the fresh water in the reservoir 807, the resultant solution is at the desired concentration for its application.

When the reservoir 807 is filled, a fluid level sensor indicates this condition to controller 814, which then disables valve 804. The following description illustrates an example of one embodiment for a batch process to make 30 gallons of $ClO_2$ solution at a final concentration of 3 to 5 parts per million. In this embodiment, the process takes approximately 30 minutes.

In this example, the inner envelope 350, containing the precursor reactants contains 1 gram of sodium chlorite and 4 grams of citric acid, enclosed within 6 square inches of membrane material. In some embodiments, the envelope comprises the membrane material. This amount of precursor chemical will completely react in approximately 30 minutes when activated by water at 110° F. In one embodiment, the flow of water into the inner envelope 350 may be regulated in some fashion to keep the flow at a rate that insures that the filling process takes the full 30 minutes so that there is water available in the reservoir 807 to absorb the chlorine dioxide that is produced. This eliminates the possibility of producing chlorine dioxide in a dry reaction vault, which could result in the escape of the gas from the apparatus 700.

In this example, the total flow of fresh water is restricted to 1 gallon per minute. This can be accomplished by numerous methods known in the art, including the use of a flow meter and metering valve, an inlet pressure regulator, or the cycling on and off of the solenoid valve.

As the process begins, the water that passes through the reaction vault 980 acts as the initiating agent that starts the chemical reaction. Due to the nature of the chemical reaction, the rate at which chlorine dioxide is produced is higher at the beginning of the reaction cycle and decreases as the chemical precursors are consumed by the reaction. This means that the concentration of chlorine dioxide in the water exiting the reaction vault is higher at the beginning of the cycle and becomes lower as the cycle proceeds. By the end of the cycle, no gas is being produced, and the water absorbs and removes the remaining chlorine dioxide from the vault.

Figure 15:
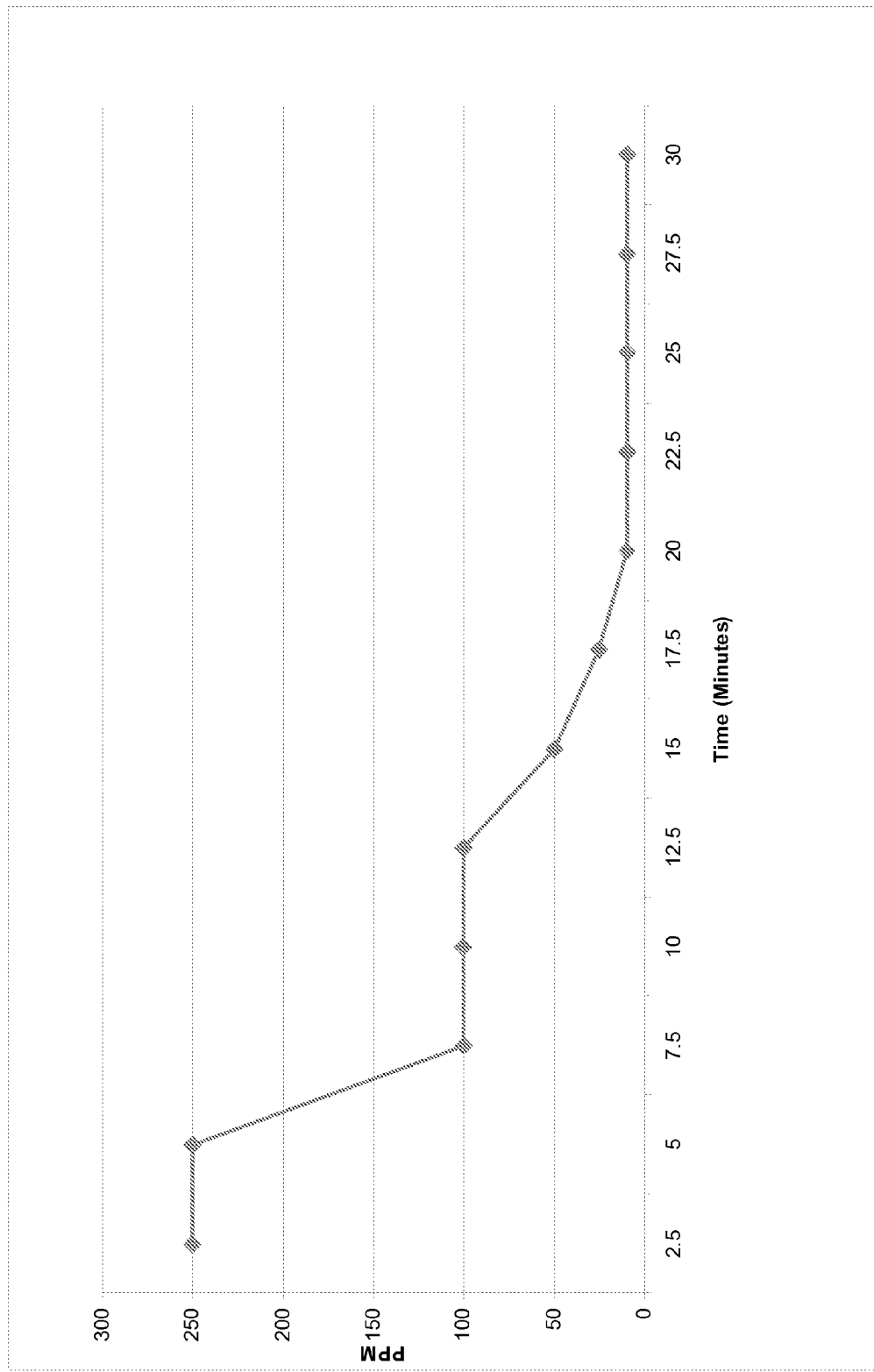
FIG. 15 shows a graph showing chlorine dioxide generation as a function of time.

The chart in FIG. 15 shows a typical concentration graph. The first reading is taken 2½ minutes after water has entered the vault, and the concentration leaving the reaction vault 980 is 250 ppm as it enters the reservoir 708. As the water enters the reservoir 708, it immediately mixes with the fresh water at a ratio of approximately 29:1, diluting the concentration to below 9 ppm. By the 7½ minute mark, the concentration in the reaction vault 980 has decreased to 100 ppm, and after about 20 minutes, it has decreased to 10 ppm, and remains at approximately that rate until the reaction has completed. At the end of the cycle, the 1 gallon of water that has passed through the reaction vault 980 and absorbed the chlorine dioxide has mixed with the 29 gallons of fresh water that went directly into the reservoir 708 to create a solution with a concentration of 3 to 5 ppm.

Once the 30 gallon cycle has been completed, the fluid level in the reservoir will cause the level indicator to signal the controller 814 that the cycle is complete, and the water flow will be stopped. Alternatively, other methods can be utilized to end the cycle, such as the use of a flow metering device to measure the amount of water that has entered the system, and stop the cycle at the appropriate time.

Figure 14:
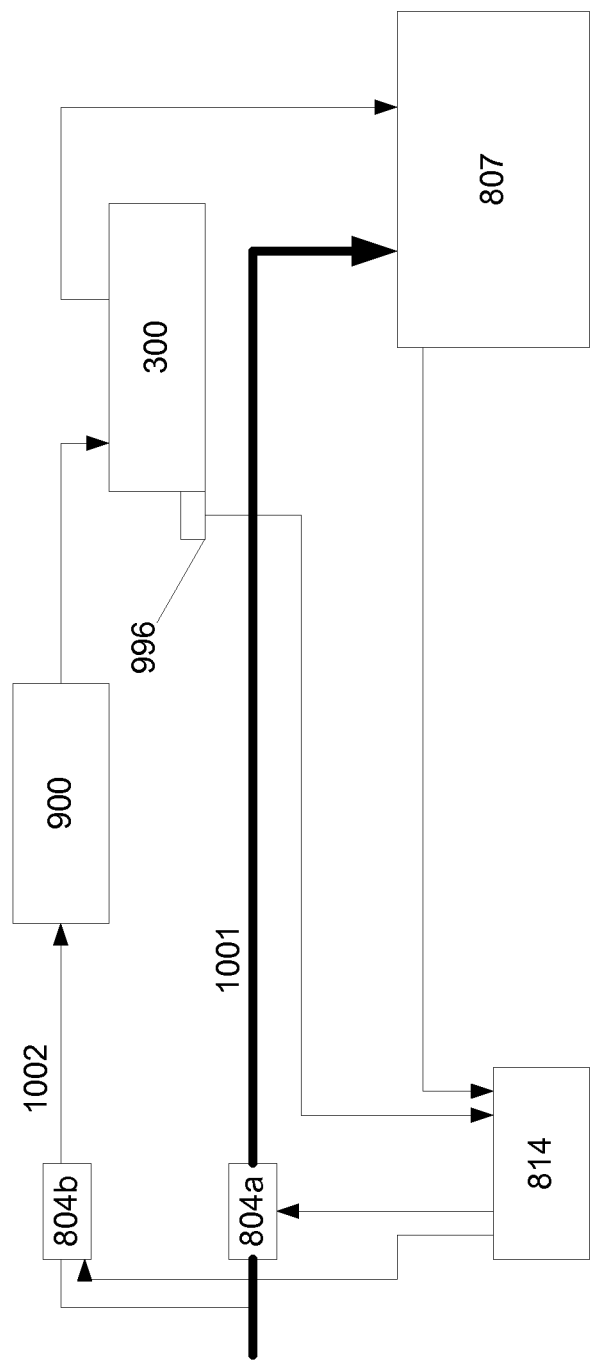
FIG. 14 shows the fluid and control paths within the apparatus according to a second embodiment.

The embodiment of FIG. 13 assumes that water simultaneously flows into the reservoir 708 and the heater 900. However, other embodiments are also possible. For example, FIG. 14 shows an embodiment where the two flows are separately controlled, such as using two separate valves 804a, 804b. In this embodiment, the fluid 1001 destined for the reservoir 807 is allowed to flow when the controller 814 opens the valve 804a. This may occur before the flow 1002 to the heater assembly 900 is enabled. In this way, there is fluid in the reservoir 807 prior to the introduction of chlorine dioxide solution from the reactor vault 980. In some embodiments, all of the fluid that is needed by the reservoir 807 flows through valve 804a, prior to the opening of valve 804b. In other embodiments, the reservoir 807 is partially filled before the valve 804b is opened. In some embodiments, a flow monitor is used to determine the amount of fluid in the reservoir 807. In other embodiments, fluid level sensors are used as described above. Once an adequate fluid level has been reached in the reservoir 807, the controller 814 opens valve 804b, thereby enabling flow 1002. As described above, water in this flow 1002 is heated by heater assembly 900, then passes through the cartridge 300 prior to entering the reservoir 807.

Figure 16:
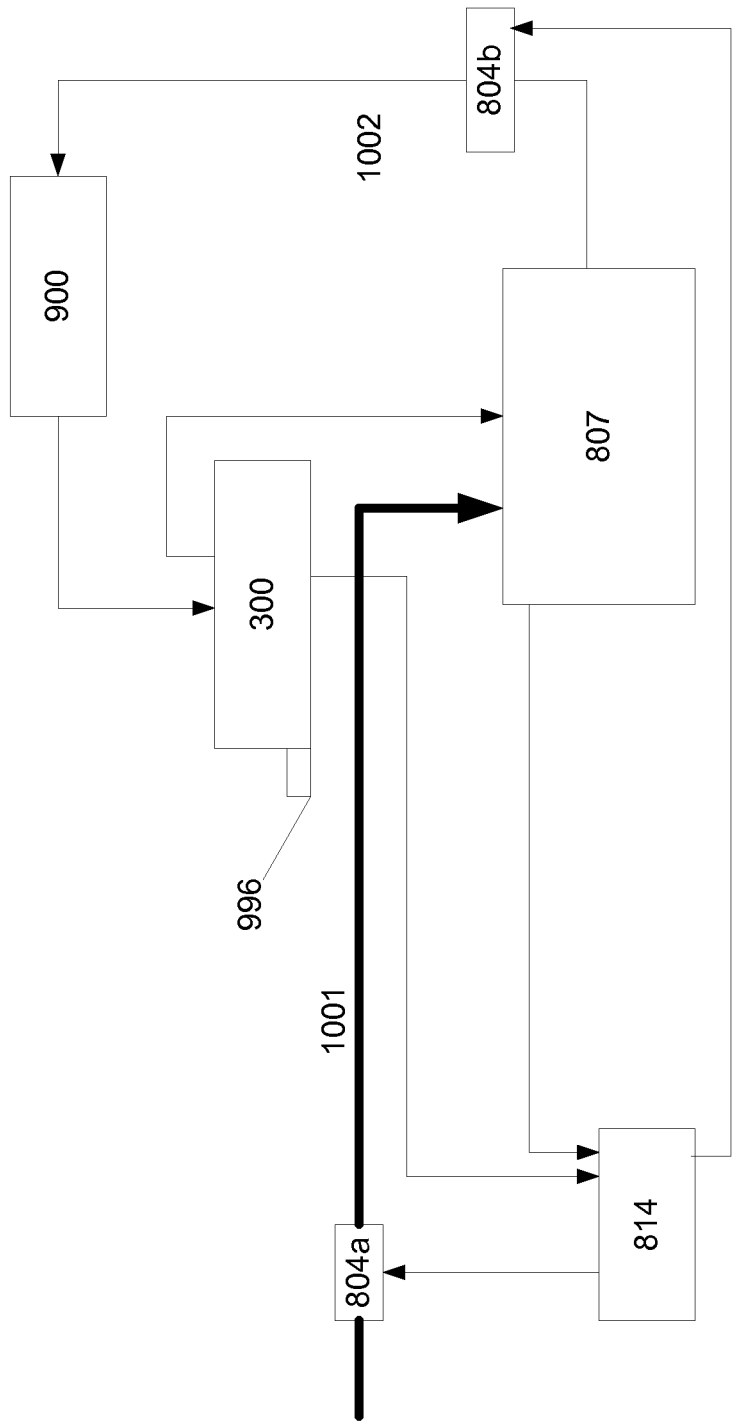
FIG. 16 shows the fluid and control paths within the apparatus according to a third embodiment.

FIG. 16 shows an embodiment in which some or all of the water is first deposited in the reservoir 807, through flow 1001. In this way, the reservoir 807 is at least partially filled prior to the introduction of chlorine dioxide solution from the reactor vault 980. In some embodiments, a flow monitor is used to determine the amount of fluid in the reservoir 807. In other embodiments, fluid level sensors are used as described above. Once an adequate fluid level has been reached in the reservoir 807, the controller 814 opens valve 804b, thereby enabling flow 1002. As described above, water in this flow 1002 may be heated by heater assembly 900, then passes through the cartridge 300 prior to reentering the reservoir 807.

Other embodiments are within the scope of this invention. Solutions of higher or lower concentrations can be created by altering the quantity of precursor chemical per final volume. The apparatus 700 can be scaled for larger or smaller batch sizes. Alternately, an apparatus 700 may be constructed with multiple reaction vaults 980. An apparatus 700 with multiple vaults can increase the total capacity without making individual cartridges 300 larger. This preserves the safety advantage of having small amounts of reactants within each cartridge 300. The multiple vaults 980 may be used in parallel, meaning that reaction water flows through all of the vaults 980, then into the reservoir 807. Alternatively, the vaults 980 may be used in series, either to make multiple small batches without the need to replace the cartridge 300 each time, or sequentially, to make one large batch by passing water through each one in a consecutive manner.

In some embodiments, it is preferred to leave some of the solution from the prior batch in the reservoir 807 when a new batch is begun. In this manner, at the beginning of a batch, the higher concentration solution that enters the reservoir 807 goes into the lower concentration solution that remains, immediately diluting it to a lower concentration. This does not affect the final concentration, since the left over solution is already at the correct concentration.

Referring to FIGS. 14 and 16, it can be seen that the controller 814 is used to control the actuation of the first valve 804a, the second valve 804b. In some embodiments, the controller 814 may also control the heating element 900, such as whether it is turned on, and if so, at what temperature. The controller 814 also has access to the fluid level in the reservoir 807 through fluid level sensors. Based on these parameters, the controller 814 can control the total volume of water taken in, the volume that is directed through the reaction chamber 300, and the temperature of the water directed through the reaction chamber. Thus, in some embodiments, the controller 814 may utilize these parameters to customize the creation of the sanitizing fluid. For example, the controller 814, through either a user interface (not shown), or via the cartridge (such as by an RFID tag), can be informed of the cartridge type. Based on the cartridge type, the controller 814 sets the temperature of the heating element 900, and actuates the valves 804*a*, 804*b* to precisely control the volume of water in the reservoir 807 and passing through the reaction chamber. In one example, the controller 814 may recognize the cartridge to be that described earlier, in which 29 gallons of water are fed to the reservoir 807, and one gallon of water, heated to 110° F. are fed through the reaction chamber.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. An apparatus for the preparation of a cleaning, sanitizing, or sterilizing solution, comprising:
   a reservoir to hold said solution;
   a first fluid path to allow incoming fluid to flow into said reservoir;
   a reaction chamber, comprising chemical precursors adapted to react with incoming fluid;
   a second fluid path to allow incoming fluid to flow to said reaction chamber;
   a third fluid path from said reaction chamber to said reservoir;
   a controller;
   and a valve,
   wherein said controller actuates said valve to enable said incoming fluid to flow into said first fluid path and said second fluid path.

2. The apparatus of claim 1, further comprising a heating element in said second fluid path, such that heated fluid enters said reaction chamber.

3. The apparatus of claim 2, wherein the temperature of said heated fluid is selected to control the reaction of the reactants at a desired rate.

4. The apparatus of claim 1, wherein said reaction chamber comprises a replaceable cartridge.

5. The apparatus of claim 1, wherein said precursors are selected from the group comprising sodium chlorite, citric acid, and combinations thereof.

6. The apparatus of claim 1, wherein said first fluid path and said second fluid paths comprise conduits, and said conduits are dimensioned to allow a predetermined fraction of said incoming fluid to enter said second fluid path.

7. The apparatus of claim 1, further comprising a pressure regulator to control the flow rate of said incoming fluid.

8. The apparatus of claim 7, wherein said first fluid path and said second fluid path comprise conduits, and said conduits are dimensioned to allow a predetermined flow rate in said second fluid path.

9. An apparatus for the preparation of a cleaning, sanitizing, or sterilizing solution, comprising:
   a reservoir to hold said solution;
   a first fluid path to allow incoming fluid to flow into said reservoir;
   a reaction chamber, comprising a replaceable cartridge and chemical precursors adapted to react with incoming fluid;
   a second fluid path to allow incoming fluid to flow to said reaction chamber; and
   a third fluid path from said reaction chamber to said reservoir;
   wherein said second fluid path terminates in a water inlet, and said third flow path begins with a water outlet, further comprising an actuator, wherein said actuator actuates said water inlet and water outlet to a first position to create a fluid path between said water inlet and said water outlet though said cartridge.

10. The apparatus of claim 9, wherein said actuator actuates said water inlet and water outlet to a second position to disrupt said fluid path between said water inlet and said water outlet though said cartridge so that said cartridge can be removed.

11. The apparatus of claim 9, further comprising a heating element in said second fluid path, such that heated fluid enters said reaction chamber.

12. The apparatus of claim 11, wherein the temperature of said heated fluid is selected to control the reaction of the reactants at a desired rate.

13. The apparatus of claim 9, wherein said precursors are selected from the group comprising sodium chlorite, citric acid, and combinations thereof.

14. An apparatus for the preparation of a cleaning, sanitizing, or sterilizing solution, comprising:
   a reservoir to hold said solution;
   a first fluid path to allow incoming fluid to flow into said reservoir;
   a reaction chamber, comprising chemical precursors adapted to react with incoming fluid;
   a second fluid path to allow incoming fluid to flow to said reaction chamber;
   a third fluid path from said reaction chamber to said reservoir;
   a controller;
   a first valve; and
   a second valve,
   such that said controller actuates first valve to enable the incoming fluid to flow into said first fluid path and actuates said second valve to enable the incoming fluid to flow into said second fluid path.

15. The apparatus of claim 14, wherein said controller actuates said second valve after actuating said first valve, such that said reservoir is at least partially filled prior to opening of said second valve.

16. The apparatus of claim 14, wherein said reaction chamber comprises a replaceable cartridge.

17. The apparatus of claim 14, wherein said precursors are selected from the group comprising sodium chlorite, citric acid, and combinations thereof.

18. The apparatus of claim 16, wherein said controller actuates said first valve and said second valve based on the type of replaceable cartridge installed in said apparatus.

19. The apparatus of claim 18, further comprising a heating element in said second fluid path, such that heated fluid enters said reaction chamber and wherein said controller controls said heating element to set the temperature of said heated fluid entering said reaction chamber.

20. The apparatus of claim 19, wherein said controller sets the temperature of said heater based on the type of replaceable cartridge installed in said apparatus.

* * * * *